United States Patent
Yang et al.

(10) Patent No.: US 8,386,247 B2
(45) Date of Patent: Feb. 26, 2013

(54) SYSTEM FOR PROCESSING AN AUDIO SIGNAL TO ENHANCE SPEECH INTELLIGIBILITY

(75) Inventors: Jun Yang, San Jose, CA (US); Richard J. Oliver, Capistrano Beach, CA (US); James Tracey, Santa Ana, CA (US); Xing He, Tustin, CA (US)

(73) Assignee: DTS LLC, Calabasas, CA (US)

( * ) Notice: Subject to any disclaimer, the term of this patent is extended or adjusted under 35 U.S.C. 154(b) by 0 days.

(21) Appl. No.: 13/525,955

(22) Filed: Jun. 18, 2012

(65) Prior Publication Data
US 2012/0259625 A1    Oct. 11, 2012

Related U.S. Application Data

(62) Division of application No. 12/559,329, filed on Sep. 14, 2009, now Pat. No. 8,204,742.

(51) Int. Cl.
*G10L 11/00* (2006.01)
*G10L 21/00* (2006.01)

(52) U.S. Cl. ........ 704/233; 704/226; 704/205; 704/209; 381/94.7; 379/391; 379/406.1

(58) Field of Classification Search .................. 704/226, 704/233, 205, 206; 381/94.7; 379/347, 406.01
See application file for complete search history.

(56) References Cited

U.S. PATENT DOCUMENTS

| | | | |
|---|---|---|---|
| 3,101,446 A | 8/1963 | Glomb et al. | |
| 3,127,477 A | 3/1964 | David, Jr. et al. | |
| 4,454,609 A * | 6/1984 | Kates | 381/320 |
| 4,882,758 A | 11/1989 | Uekawa et al. | |
| 5,175,769 A | 12/1992 | Hejna, Jr. et al. | |
| 5,471,527 A | 11/1995 | Ho et al. | |
| 5,524,148 A * | 6/1996 | Allen et al. | 379/391 |
| 5,537,479 A | 7/1996 | Kreisel et al. | |
| 5,550,924 A * | 8/1996 | Helf et al. | 381/94.3 |
| 5,677,987 A | 10/1997 | Seki et al. | |
| 5,742,689 A | 4/1998 | Tucker et al. | |
| 5,966,689 A | 10/1999 | McCree | |
| 6,064,962 A | 5/2000 | Oshikiri et al. | |
| 6,510,224 B1 * | 1/2003 | Christensson et al. | 379/406.03 |
| 6,704,711 B2 | 3/2004 | Gustafsson et al. | |
| 6,741,873 B1 * | 5/2004 | Doran et al. | 455/569.1 |
| 6,766,176 B1 | 7/2004 | Gupta et al. | |
| 6,993,480 B1 | 1/2006 | Klayman | |
| 7,152,032 B2 | 12/2006 | Suzuki et al. | |
| 7,242,763 B2 * | 7/2007 | Etter | 379/406.14 |

(Continued)

OTHER PUBLICATIONS

International Preliminary Report on Patentability issued in application No. PCT/US2009/053437 on Feb. 14, 2012.
International Search Report and Written Opinion in PCT/US2009/056850, Nov. 2, 2009.

(Continued)

*Primary Examiner* — Jialong He
(74) *Attorney, Agent, or Firm* — Knobbe Martens Olson & Bear LLP

(57) ABSTRACT

An adaptive audio system can be implemented in a communication device. The adaptive audio system can enhance voice in an audio signal received by the communication device to increase intelligibility of the voice. The audio system can adapt the audio enhancement based at least in part on levels of environmental content, such as noise, that are received by the communication device. For higher levels of environmental content, for example, the audio system might apply the audio enhancement more aggressively. Additionally, the adaptive audio system can detect substantially periodic content in the environmental content. The adaptive audio system can further adapt the audio enhancement responsive to the environmental content.

16 Claims, 16 Drawing Sheets

U.S. PATENT DOCUMENTS

| | | | |
|---|---|---|---|
| 7,349,841 B2 | 3/2008 | Furuta et al. | |
| 7,424,423 B2 | 9/2008 | Bazzi et al. | |
| 8,254,590 B2 * | 8/2012 | Taenzer | 381/73.1 |
| 2002/0172350 A1 * | 11/2002 | Edwards et al. | 379/392.01 |
| 2004/0057586 A1 | 3/2004 | Licht | |
| 2004/0071284 A1 | 4/2004 | Abutalebi et al. | |
| 2004/0078200 A1 | 4/2004 | Alves | |
| 2005/0065781 A1 | 3/2005 | Tell et al. | |
| 2005/0075864 A1 | 4/2005 | Kim | |
| 2005/0086058 A1 * | 4/2005 | Lemelson et al. | 704/270 |
| 2005/0246170 A1 | 11/2005 | Vignoli et al. | |
| 2006/0130637 A1 | 6/2006 | Crewbouw | |
| 2007/0025480 A1 | 2/2007 | Tackin et al. | |
| 2007/0118363 A1 | 5/2007 | Sasaki et al. | |
| 2007/0134635 A1 | 6/2007 | Hardy et al. | |
| 2008/0022009 A1 | 1/2008 | Yuen et al. | |
| 2008/0228473 A1 | 9/2008 | Kinoshita | |
| 2008/0232612 A1 | 9/2008 | Tourwe | |
| 2008/0249772 A1 | 10/2008 | Martynovich et al. | |
| 2008/0312916 A1 * | 12/2008 | Konchitsky et al. | 704/226 |
| 2009/0112579 A1 | 4/2009 | Li et al. | |
| 2009/0281805 A1 * | 11/2009 | LeBlanc et al. | 704/233 |

OTHER PUBLICATIONS

International Search Report and Written Opinion in PCT/US2009/053437, Oct. 2, 2009.

Anderton, Craig, "DC Offset: The Case of the Missing Headroom" Harmony Central. http://www.harmonycentral.com/docs/DOC-1082, Apr. 19, 2010.

SCM Repositories—SND Revision 1.2, Jul. 21, 2007, SourceForge, Inc.

Roger Derry, PC Audio Editing with Adobe Audition 2.0 Broadcast, desktop and CD audio production, First edition 2006, Eisever Ltd.

P1 Audio Processor, White Paper, May 2003, Safe Sound Audio 2003.

Khalil C. Haddad, et al., Design of Digital Linear-Phase FIR Crossover Systems for Loudspeakers by the Method of Vector Space Projections, Nov. 1999, vol. 47, No. 11, pp. 3058-3066.

Schottstaedt, SCM Repositories—SND Revision 1.2, Jul. 21, 2007, SourceForge, Inc.

Hu et al. "A Perceptually Motivated Approach for Speech Enhancement", IEEE Transactions on Speech and Audio Processing, vol. 11, No. 5, Sep. 2003.

* cited by examiner

US 8,386,247 B2

SYSTEM FOR PROCESSING AN AUDIO SIGNAL TO ENHANCE SPEECH INTELLIGIBILITY

RELATED APPLICATION

This application is a divisional of U.S. patent application Ser. No. 12/559,329, filed Sep. 14, 2009, and issuing on Jun. 19, 2012 as U.S. Pat. No. 8,204,742, which is hereby incorporated herein by reference in its entirety.

BACKGROUND

Description of the Related Technology

Mobile phones are often used in areas that include high background noise. This noise is often of such a level that intelligibility of the spoken communication from the mobile phone speaker is greatly degraded. In many cases, some communication is lost or at least partly lost because high ambient noise level masks or distorts a caller's voice, as it is heard by the listener.

Attempts to minimize loss of intelligibility in the presence of high background noise have involved use of equalizers, clipping circuits, or simply increasing the volume of the mobile phone. Equalizers and clipping circuits can themselves increase background noise, and thus fail to solve the problem. Increasing the overall level of sound or speaker volume of the mobile phone often does not significantly improve intelligibility and can cause other problems such as feedback and listener discomfort.

SUMMARY OF THE DISCLOSURE

In certain embodiments, a system for automatically adjusting a voice intelligibility enhancement applied to an audio signal includes an enhancement module that can receive an input voice signal comprising formants and apply an audio enhancement to the input voice signal to provide an enhanced voice signal. The audio enhancement can emphasize one or more of the formants in the input voice signal. The system can further include an enhancement controller having one or more processors. The enhancement controller can adjust the amount of the audio enhancement applied by the enhancement module based at least partly on an amount of detected environmental noise. The system can further include an output gain controller that can adjust an overall gain of the enhanced voice signal based at least partly on the amount of environmental noise and the input voice signal, and apply the overall gain to the enhanced voice signal to produce an amplified voice signal. The system can further include a distortion control module that can reduce clipping in the amplified voice signal by at least mapping one or more samples of the amplified voice audio signal to one or more values stored in a sum of sines table. The sum of sines table can be generated from a sum of lower-order sine harmonics.

In various embodiments, a method of adjusting a voice intelligibility enhancement can include receiving a voice signal and an input signal having near-end environmental content, calculating with one or more processors the near-end environmental content in the input signal, adjusting with the one or more processors a level of a voice enhancement based at least partly on the near-end environmental content, and applying the voice enhancement to the voice signal to produce an enhanced voice signal. The voice enhancement can emphasize one or more formants of the voice signal.

Additionally, in certain embodiments, a system for automatically adjusting a voice intelligibility enhancement applied to an audio signal can include an enhancement module that can receive an input voice signal having formants and apply an audio enhancement to the input voice signal to provide an enhanced voice signal. The audio enhancement can emphasize one or more of the formants in the input voice signal. The system can further include an enhancement controller including one or more processors. The enhancement controller can adjust the amount of the audio enhancement applied by the enhancement module based at least partly on an amount of detected environmental noise. The system can further include an output gain controller that can adjust an overall gain of the enhanced voice signal based at least partly on the amount of environmental noise and on the input voice signal and apply the overall gain to the enhanced voice signal to produce an amplified voice signal.

A processor-readable storage medium having instructions stored thereon that cause one or more processors to perform a method of adjusting a voice intelligibility enhancement can include: receiving a voice signal from a remote phone and a noise signal from a microphone, calculating a value of the noise signal, adjusting gains applied to formants of the voice signal based at least partly on the value of the noise signal, and applying the gains to the formants of the voice signal.

In some implementations, a system for adjusting a noise threshold of a voice intelligibility enhancement can include a voice enhancement module that can receive, with a receiving device, an input voice signal from a remote device and to apply an audio enhancement to the input voice signal to emphasize one or more of the formants in the input voice signal. The system can further include a voice enhancement controller having one or more processors. The voice enhancement controller can adjust the amount of the audio enhancement applied by the enhancement module based at least partly on an amount of detected environmental noise above a first noise threshold. The system can further include a noise sensitivity controller that can adjust the first noise threshold. The noise sensitivity controller can include a first correlator that can compute first autocorrelation values from a microphone input signal received from a microphone of the receiving device, a first variance module that can compute a first variance of the first autocorrelation values, a second correlator that can compute second autocorrelation values from a speaker input signal, where the speaker input signal includes an output signal of the voice enhancement module, a second variance module that can compute a second variance of the second autocorrelation values, and a noise sensitivity adjuster that can use one or more of the first and second autocorrelation values and the first and second variance values to adjust the first noise threshold to produce a second noise threshold. Thus, in certain embodiments, the voice enhancement controller can adjust the amount of audio enhancement applied to a second input audio signal based at least partly on a second amount of detected environmental noise above the second noise threshold.

A system for adjusting a sensitivity of a voice intelligibility enhancement includes, in certain embodiments, a voice enhancement module that can receive, with a receiving device, an input voice signal received by a receiving device from a remote device and apply an audio enhancement to the input voice signal to emphasize one or more of the formants in the input voice signal. The system can further include an enhancement controller that can adjust the amount of the audio enhancement applied by the voice enhancement module based at least partly on an amount of environmental noise present in the input voice signal. The system can further include a noise sensitivity controller having one or more processors that can adjust a sensitivity of the enhancement controller to the environment noise based at least partly on a statistical analysis of at least one or both of a microphone input signal obtained from a microphone of the receiving device and a speaker input signal provided as an output signal of the voice enhancement module.

In certain embodiments, a method for adjusting a sensitivity of a voice enhancement includes: receiving an input audio signal, detecting correlated content in the input audio signal, where detecting includes using one or more processors to compute a statistical analysis of the input audio signal, and in response to performing the detecting, adjusting a level of an enhancement applied to the input audio signal.

Moreover, in various embodiments, an audio signal processing method includes receiving a microphone input signal, detecting substantially periodic content in the microphone input signal, and adjusting an audio enhancement with one or more processors based at least in part on the substantially periodic content detected in the microphone input signal. The audio enhancement can selectively enhance an audio output signal based at least in part on a level of the microphone input signal. The method can further include providing the audio output signal to a speaker.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers can be reused to indicate correspondence between referenced elements. The drawings are provided to illustrate embodiments of the inventions described herein and not to limit the scope thereof.

DETAILED DESCRIPTION

I. Introduction

Mobile phones and other similar-sized devices tend to have small speakers that are limited in the volume of sound they produce. In the presence of environmental noise, it can therefore be difficult to hear a conversation on a mobile phone.

This disclosure describes systems and methods for adapting voice intelligibility processing based on environmental noise, speech levels, combinations of the same, and the like. Voice intelligibility processing can include techniques of emphasizing formants in speech. The voice intelligibility processing can be used, for example, to clarify speech in a mobile phone conversation or the like. The voice intelligibility processing can be adapted to increase or decrease the emphasis of voice formants and other vocal characteristics based at least in part on environmental noise. By increasing the voice intelligibility processing, formants in the speaker's speech can be emphasized so as to be more clearly perceived by a listener. However, in the absence of significant environmental noise, emphasizing the formants in speech can cause the speech to sound harsh. Thus, if the environmental noise decreases, the amount of voice intelligibility processing can be decreased to avoid harshness in the speech.

In addition, the overall gain of the audio signal can also be increased adaptively based at least partly on the noise level and/or voice level. If the gain of the audio signal is increased beyond a certain level, however, saturation of the audio signal can occur, causing harmonic distortion. To reduce the distortive effects of saturation, in certain embodiments a distortion control process can be used. The distortion control process can reduce distortion that occurs during high gain situations while allowing some distortion to occur to preserve or increase loudness. Distortion control can be performed in certain embodiments by mapping the audio signal to an output signal that has fewer harmonics than a fully-saturated signal.

II. System Overview

Figure 1:
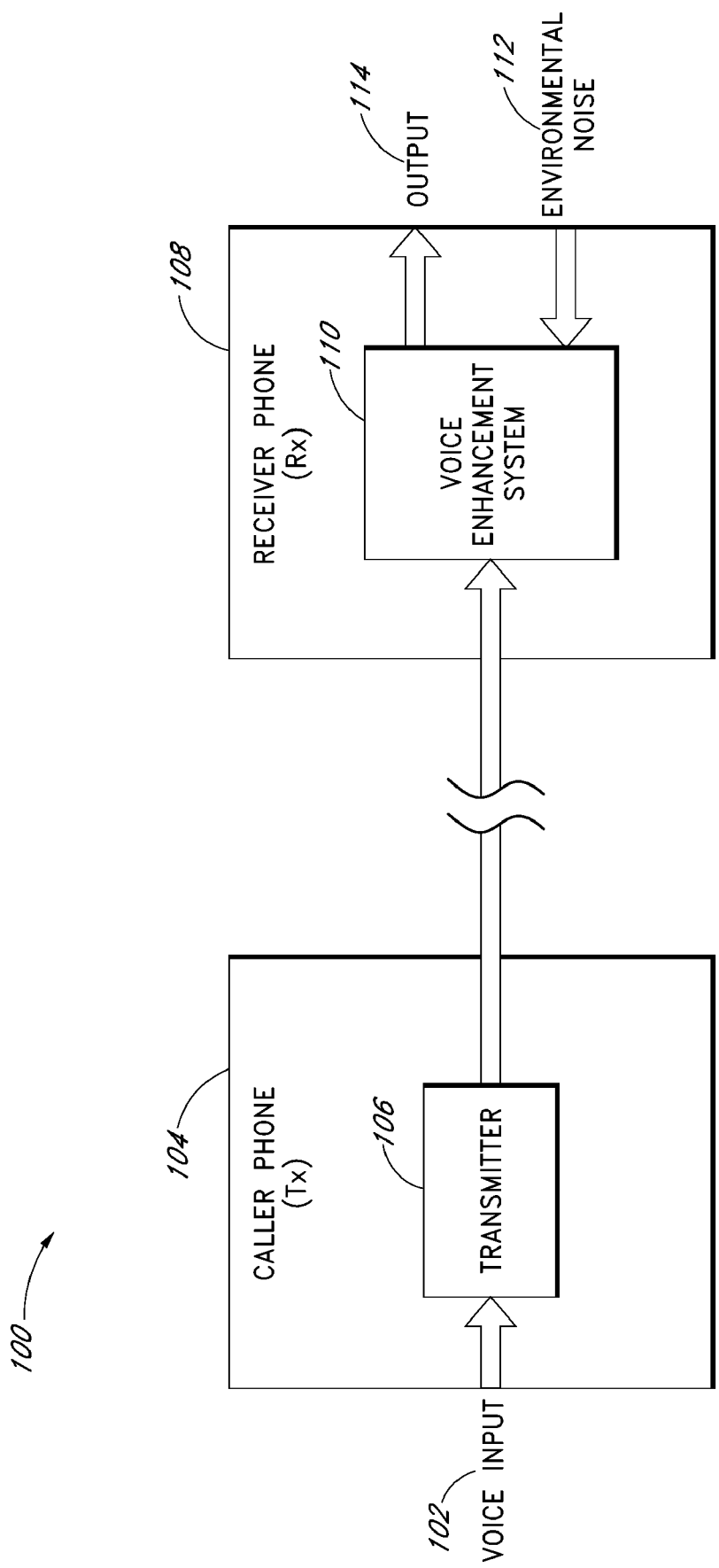
FIG. 1 illustrates an embodiment of a mobile phone environment for implementing a voice enhancement system.

FIG. 1 illustrates an embodiment of a mobile phone environment 100 for implementing a voice enhancement system 110. In the example mobile phone environment 100, a caller phone 104 and a receiver phone 108 are shown. The caller phone 104 and the receiver phone 108 can be mobile phones, voice over Internet protocol (VoIP) phones, smart phones, landline phones, or the like. The caller phone 104 can be considered to be at the far-end of the mobile phone environment 100, and the receiver phone can be considered to be at the near-end of the mobile phone environment 100. When the user of the receiver phone 108 is speaking, the near and far-ends can reverse.

In the depicted embodiment, a voice input 102 is provided to the caller phone 104 by a caller. A transmitter 106 in the caller phone 104 transmits the voice input signal 102 to the receiver phone 108. The transmitter 106 can transmit the voice input signal 102 wirelessly or through landlines, depending on the type of the caller phone 104. A voice enhancement system 110 of the receiver phone 108 can receive the voice input signal 102. The voice enhancement system 110 can include hardware and/or software for increasing the intelligibility of the voice input signal 102. The voice enhancement system 110 can, for example, process the voice input signal 102 with a voice enhancement that emphasizes distinguishing characteristics of vocal sounds.

The voice enhancement system 110 can also detect environmental noise 112 using a microphone of the receiver phone 108. The environmental noise or content 112 can include background or ambient noise. In addition to its ordinary meaning, environmental noise or content can also include some or all near-end sounds. For instance, in addition to background sounds received by the microphone of the receiver phone 108, the environmental noise or content can include echo from a speaker output 114. The environmental noise could, in some instances, also include voice input from the user of the receiver phone 108, including coughing, throat clearing, and double talk (see "Noise Sensitivity Control" section below).

Advantageously, in certain embodiments, the voice enhancement system 110 adapts a degree to which the voice enhancement is applied to the voice input signal 102 based at least partly on the amount of environmental noise 112. For instance, if the environmental noise 112 increases, the voice enhancement system 110 can increase the amount of the voice enhancement applied, and vice versa. The voice enhancement can therefore at least partly track the amount of detected environmental noise 112.

In addition, the voice enhancement system 110 can increase an overall gain applied to the voice input signal 102 based at least partly on the amount of environmental noise 112. However, when less environmental noise 112 is present, the voice enhancement system 110 can reduce the amount of the voice enhancement and/or gain increase applied. This reduction can be beneficial to the listener because the voice enhancement and/or volume increase can sound harsh or unpleasant when there are low levels of background noise 112.

Thus, in certain embodiments, the voice enhancement system 110 transforms the voice input signal into an enhanced output signal 114 that can be more intelligible to a listener in the presence of varying levels of environmental noise. In some embodiments, the voice enhancement system 110 can also be included in the caller phone 104. The voice enhancement system 110 might apply the enhancement to the voice input signal 102 based at least partly on an amount of environmental noise detected by the caller phone 104. The voice enhancement system 110 can therefore be used in the caller phone 104, the receiver phone 108, or both.

Although the voice enhancement system 110 is shown being part of the phone 108, the voice enhancement system 110 could instead be implemented in any communication device or in a device that communicates with a phone. For instance, the voice enhancement system 110 could be implemented in a computer, router, analog telephone adapter, or the like that communicates with or is coupled with a VoIP-enabled phone. The voice enhancement system 110 could also be used in Public Address ("PA") equipment (including PA over Internet Protocol), radio transceivers, assistive hearing devices (e.g., hearing aids), speaker phones, and in other audio systems. Moreover, the voice enhancement system 110 can be implemented in any processor-based system that provides an audio output to one or more speakers.

Figure 2:
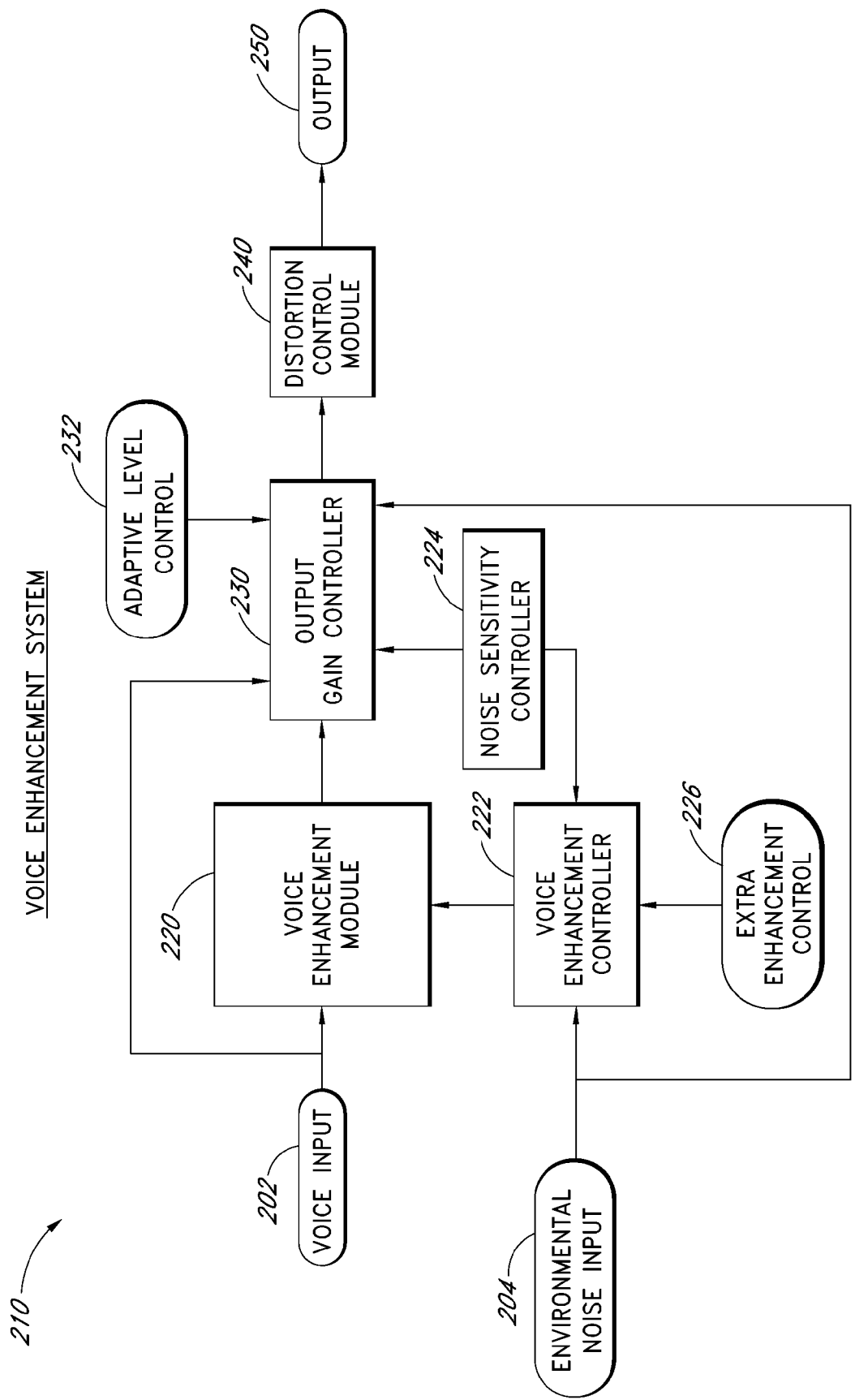
FIG. 2 illustrates an embodiment of the voice enhancement system of FIG. 1.

FIG. 2 illustrates a more detailed embodiment of a voice enhancement system 210. The voice enhancement system 210 can have all the features of the voice enhancement system 110. The voice enhancement system 210 can be implemented in a mobile phone, cell phone, smart phone, or other computing device, including any of the devices mentioned above. Advantageously, in certain embodiments, the voice enhancement system 210 adapts voice intelligibility processing and volume processing based at least partly on a detected amount of environmental noise and/or a level of a voice signal.

The voice enhancement system 210 includes a voice enhancement module 220. The voice enhancement module 220 can include hardware and/or software for applying a voice enhancement to a voice input signal 202. The voice enhancement can emphasize distinguishing characteristics of vocal sounds in the voice input signal 202. In certain embodiments, these distinguishing characteristics include formants produced in a vocal tract of a person (e.g., a caller using a phone). Intelligibility of the human voice can largely depend on the pattern of frequency distribution of the formants. Therefore, the voice enhancement module 220 can selectively enhance the formants to provide more understandable speech in the presence of background noise.

In certain embodiments, the voice enhancement module 220 applies the voice enhancement using some or all of the features described in U.S. Pat. No. 5,459,813, issued Oct. 17, 1995, titled "Public Address Intelligibility System" ("the '813 patent"), the disclosure of which is hereby incorporated by reference in its entirety. Although the '813 patent describes these features in the context of circuits, the voice enhancement module 220 can implement some or all of these features using instructions executed in a processor, such as a digital signal processor (DSP). Additionally, the voice enhancement module 220 can also use voice enhancement techniques not disclosed in the '813 patent.

The voice enhancement module 220 can process formants by dividing the voice input signal 202 into frequency sub-bands. The voice enhancement module 220 can divide the voice input signal 202 into two or more sub-bands, or the like. The voice enhancement module 220 can perform this frequency division by applying band-pass filters having center frequencies where formants tend to occur or near where formants tend to occur. In an embodiment, this frequency division can be accomplished by the spectrum analyzer 42 or 124 of the '813 patent (or a digital implementation thereof), described, for example, in column 4, line 50 to column 5, line 24 and in column 7, lines 10 through 32, which portions of the '813 patent are hereby specifically incorporated by reference herein.

The voice enhancement module 220 can apply the voice enhancement by individually amplifying and selectively weighting the formants in the sub-bands. Weighting the formants can cause certain formants to be emphasized, thereby increasing intelligibility. The voice enhancement module 220 can combine the weighted formants with a baseband voice component to provide an output voice signal to an output gain controller 230 (described below). The voice enhancement module 220 can also enhance other vocal distinguishing characteristics, such as plosives and fricatives.

The voice enhancement module 220 can perform these amplification, weighting, and combining functions in the same or similar manner as described in the '813 patent (or a digital implementation thereof), for example, at column 5, lines 1-7; column 5 line 46 through column 6, line 19; and column 9, lines 8 through 39. These portions of the '813 patent are hereby specifically incorporated by reference herein. To illustrate an example of how certain of these functions might be implemented digitally, the '813 patent describes weighting the signals in certain sub-bands using variable resistors (see, e.g., column 5, line 66 through column 6, line 19). The voice enhancement module 220 can implement these weights digitally by storing gain values in a memory and applying the gain values to a signal using a processor.

Advantageously, in certain embodiments, a voice enhancement controller 222 is provided that can control the level of the voice enhancement provided by the voice enhancement module 220. The voice enhancement controller 222 can include hardware and/or software. The voice enhancement controller 222 can provide an enhancement level control signal or value to the voice enhancement module 220 that increases or decreases the level of the voice enhancement applied. In one embodiment, the enhancement level control signal adjusts the weighting of the sub-bands. For example, the control signal could include one or more gain values that multiply the output (or input) of some or all of the sub-bands. Likewise, the control signal could be used to add or subtract from the input or output of some or all sub-bands. The control signal can adapt sample by sample as the environment noise 204 increases and decreases.

In certain embodiments, the voice enhancement controller 222 adapts the level of the voice enhancement after a threshold amount of energy of the environmental noise 204 is detected. Above the threshold, the voice enhancement controller 222 can cause the level of the voice enhancement to track or substantially track the amount of environmental noise 204. In one embodiment, for example, the level of the voice enhancement provided above the noise threshold is proportional to a ratio of the energy (or power) of the noise to the threshold. In alternative embodiments, the level of the voice enhancement is adapted regardless of the amount of environmental noise present, for example, without using a threshold.

The depicted embodiment of the voice enhancement system 210 includes a noise sensitivity controller 224 and an extra enhancement control 226 for further adjusting the amount of control provided by the voice enhancement controller 222. The noise sensitivity controller 224 can provide a noise sensitivity control value to the voice enhancement controller 222 to adjust how sensitive the voice enhancement controller 222 is to the amount of noise 204 present. As will be described below in more detail, the noise sensitivity controller 224 can affect a noise threshold, below which the voice enhancement controller 222 cannot adjust the level of the voice enhancement.

In certain embodiments, the noise sensitivity controller 224 generates the noise sensitivity control automatically based at least partly on audio samples obtained from microphone and/or speaker inputs. Advantageously, in certain embodiments, the noise sensitivity controller 224 can automatically adjust the noise sensitivity to account for speaker echo picked up by a microphone and for other noise artifacts. These features are described in greater detail below with respect to FIGS. 5 and 6. In addition, in some embodiments, the noise sensitivity controller 224 provides a user interface that allows a user to adjust the noise sensitivity control. Thus, the noise sensitivity controller 224 can provide automatic and/or manual control of the voice enhancement controller 222.

The extra enhancement control 226 can provide an extra enhancement control signal to the voice enhancement controller 222 that can be used as a value below which the enhancement level cannot go below. The extra enhancement control 226 can be exposed to a user via a user interface. This control 226 might also allow a user to increase the enhancement level beyond that determined by the voice enhancement controller 222. In one embodiment, the voice enhancement controller 222 can add the extra enhancement from the extra enhancement control 226 to the enhancement level determined by the voice enhancement controller 222. The extra enhancement control 226 might be particularly useful for the hearing impaired who can want more voice enhancement processing or want voice enhancement processing to be applied frequently.

In certain embodiments, the output gain controller 230 can control the amount of overall gain applied to the output signal of the voice enhancement module 220. The output gain controller 230 can be implemented in hardware and/or software. The output gain controller 230 can adjust the gain applied to the output signal based at least partly on the level of the noise input 204 and on the level of the voice input 202. This gain can be applied in addition to any user-set gain, such as a volume control of phone. Advantageously, adapting the gain of the audio signal based on the environmental noise 204 and/or voice input 202 level can help a listener further perceive the voice input signal 202.

An adaptive level control 232 is also shown in the depicted embodiment, which can further adjust the amount of gain provided by the output gain controller 230. A user interface could also expose the adaptive level control 232 to the user. Increasing this control 232 can cause the gain of the controller 230 to increase more as the incoming voice input 202 level decreases or as the noise input 204 increases. Decreasing this control 232 can cause the gain of the controller 230 to increase less as the incoming voice input signal 202 level decreases or as the noise input 204 decreases.

In some cases, the gains applied by the voice enhancement module 220, the voice enhancement controller 222, and/or the output gain controller 230 can cause the voice signal to clip or saturate. Saturation can result in harmonic distortion that is unpleasant to a listener. Thus, in certain embodiments, a distortion control module 140 is also provided. The distortion control module 140 can receive the gain-adjusted voice signal of the output gain controller 230. The distortion control module 140 can include hardware and/or software that controls the distortion while also at least partially preserving or even increasing the signal energy provided by the voice enhancement module 220, the voice enhancement controller 222, and/or the output gain controller 230.

In certain embodiments, the distortion control module 140 controls distortion in the voice signal by mapping one or more samples of the voice signal to an output signal having fewer harmonics than a fully-saturated signal. This mapping can track the voice signal linearly or approximately linearly for samples that are not saturated. For samples that are saturated, the mapping can be a nonlinear transformation that applies a controlled distortion. As a result, in certain embodiments, the distortion control module 140 can allow the voice signal to sound louder with less distortion than a fully-saturated signal. Thus, in certain embodiments, the distortion control module 140 transforms data representing a physical voice signal into data representing another physical voice signal with controlled distortion.

III. Voice Enhancement Control

Figure 3:
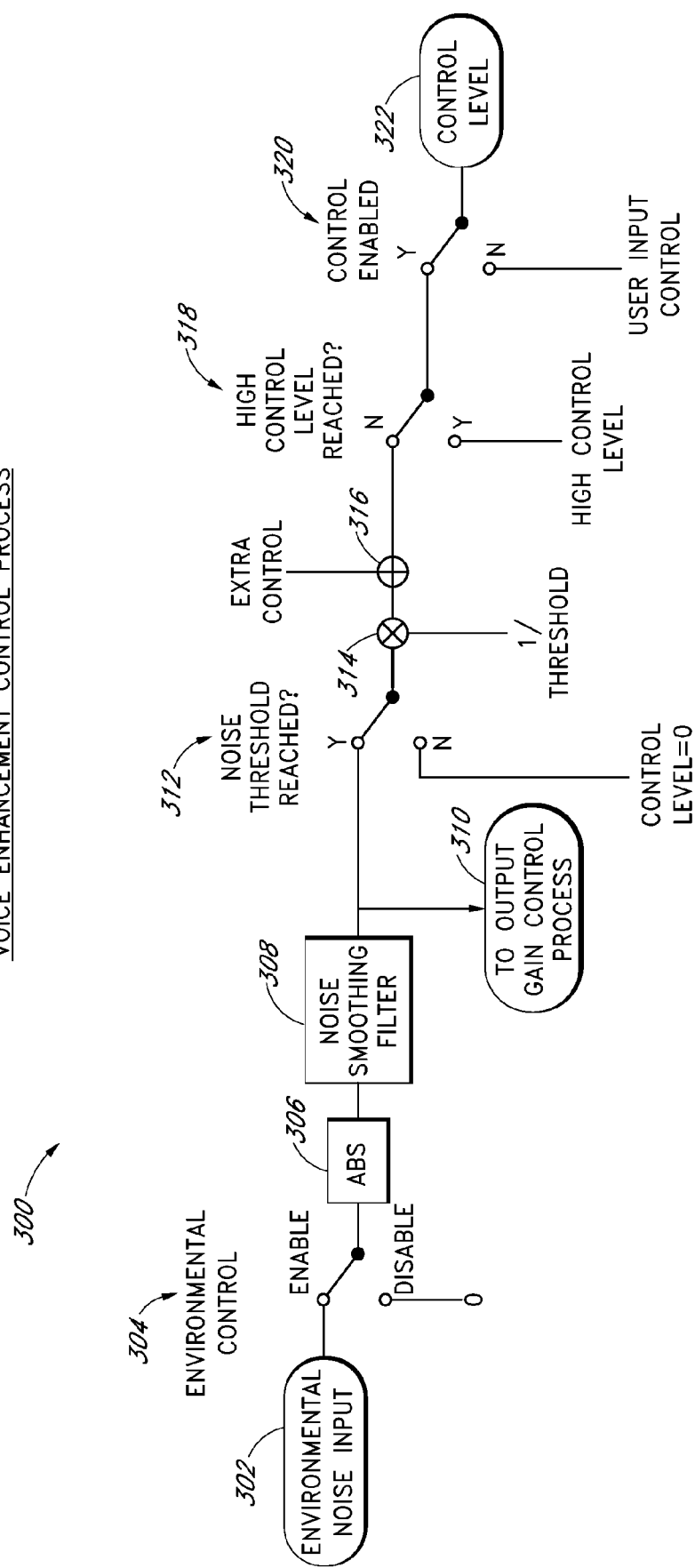
FIG. 3 illustrates an embodiment of a voice enhancement control process used by the voice enhancement system.

FIG. 3 illustrates an embodiment of a voice enhancement control process 300. The voice enhancement control process 300 can be implemented by the voice enhancement system 110 or 210. In particular, the voice enhancement control process 300 can be implemented by the voice enhancement controller 222. Advantageously, in certain embodiments, the voice enhancement control process 300 adapts voice enhancement processing based at least partly on a level of environmental noise energy.

An environmental noise input signal is received at block 302 by a communication device such as a phone. The environmental noise input signal can be detected by a microphone of the communication device. At decision block 304, it is determined whether an environmental control is enabled. If not, a value of zero can be provided to block 306. The environment control can be enabled or disabled by a user in one embodiment from a user interface of the communication device. Disabling the environmental control can cause the voice enhancement control process to adjust voice enhancement processing based on factors other than noise level, such as the extra control level described above.

The energy in the environmental noise signal can be computed at block 306 by taking the absolute value of the noise signal and at block 308 by applying a noise smoothing filter to the noise signal. The noise smoothing filter can be a first-order filter or a higher order filter. For example, the smoothing filter can be a low pass filter or the like. In some embodiments, the smoothing filter can provide an average (e.g., moving average) noise energy level on a sample per sample basis. In alternative embodiments, the power of the noise signal is calculated instead of the energy.

The energy of the environmental noise signal can be provided to an output gain control process at block 310. An example output gain control process is described below with respect to FIG. 4. The environmental noise energy can also be provided to decision block 312, which can determine whether the energy has reached (e.g., is greater than or equal) a noise threshold. In one embodiment, the noise threshold is calculated as follows:

$$\text{noise threshold} = 1 - (\alpha * \text{noise sensitivity control}) \quad (1)$$

where $\alpha$ is a constant and where the noise sensitivity control can be a value generated by the noise sensitivity controller 224 of FIG. 2. The noise sensitivity control can influence the voice enhancement controller's 222 sensitivity to the environmental noise input 302. The noise sensitivity control can vary based on a variety of factors, causing the noise threshold to vary (see FIGS. 5 and 6). In an embodiment, both a and the noise sensitivity control can range between [0, 1], or they can have other values outside this example range.

In the depicted embodiment, if the noise energy is greater than or equal to the threshold, the noise energy is passed to multiplication block 314. Otherwise, a control level of zero is provided to the multiplication block 314. Because the control level can multiply the voice signal sub bands described above with respect to FIG. 2, a control level of zero could result in potentially no voice enhancement processing being applied to the voice signal (e.g., if no extra processing is provided at block 316 below).

At multiplication block 314, the output of the decision block 312 is multiplied by the multiplicative inverse of the noise threshold. Alternatively, the output of the decision block 312 is divided by the noise threshold. The output of the multiplication block 314 can be a preliminary enhancement level. Thus, in certain embodiments, the enhancement level can be a ratio of the noise energy to the noise threshold.

At block 316, the extra enhancement control described above with respect to FIG. 2 can be added to the preliminary enhancement control level. The extra enhancement control can range from [0,1] or have some other value. At decision block 318, it is determined whether a high control level has been reached. The high control level can be a predetermined peak or maximum control level. If the high control level has been reached, the enhancement control level can be limited to the high control level at decision block 318. Otherwise, the decision block 318 passes the enhancement control level to decision block 320.

At decision block 320, it can be determined whether the voice enhancement control is enabled. If not, a user input can be used to adjust the voice enhancement processing level. The user input can be exposed to a user via a user interface or the like. If the control is enabled, the enhancement control level calculated in block 302 through 318 can be provided as an output control level at block 322.

Although a noise threshold has been used in the present example, the noise threshold need not be used in all embodiments. Voice enhancement processing can be adapted based on any level of noise in certain embodiments. However, using a threshold can be beneficial in some situations. For example, the voice enhancement processing can be harsh or unpleasant in low environmental noise situations. Thus, using a threshold to determine when to turn on the voice enhancement control can cause voice enhancement processing to be used when more significant noise levels are present.

IV. Output Gain Control

Figure 4:
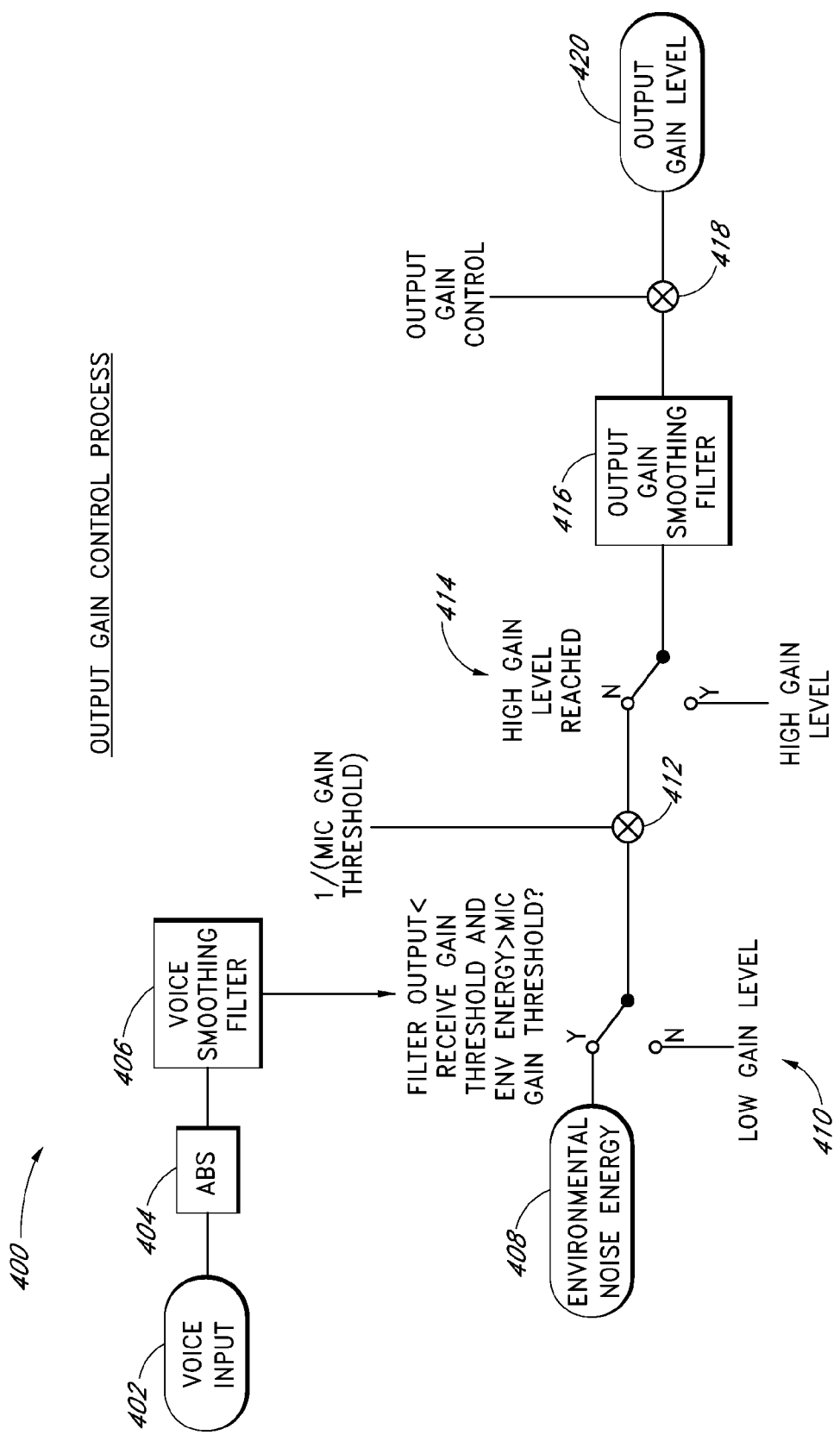
FIG. 4 illustrates an embodiment of an output volume control process used by the voice enhancement system.

FIG. 4 illustrates an embodiment of an output gain control process 400. The output gain control process 400 can be implemented by the voice enhancement system 110 or 210. In particular, the output gain control process 400 can be implemented by the output gain controller 230. Advantageously, in certain embodiments, the output gain control process 400 adapts an output gain based at least partly on a level of environmental noise energy and a voice input level.

At block 402, a voice input signal is received by a communication device such as a phone from a remote caller. At blocks 404 and 406, energy in the voice input signal is determined by taking the absolute value of the voice input at block 404 and by applying a voice smoothing filter at block 406. The voice smoothing filter can be a low pass filter or the like that provides an average (e.g., moving average) voice level on a sample per sample basis.

Environmental noise energy is received at block 408. This environmental noise energy was calculated in the volume control process 300 described above. At decision block 410, the output of the voice smoothing filter is compared to a receive gain threshold and the environmental noise energy is compared to a microphone gain threshold. The receive gain threshold can depend at least partly on the adaptive gain control described above with respect to FIG. 2. The microphone gain threshold can depend at least partly on the noise sensitivity control described above with respect to FIG. 2.

In one embodiment, the receive gain threshold is calculated as follows:

$$\text{receive gain threshold} = 0.5 + (\gamma * \text{adaptive gain control}) \quad (2)$$

where $\gamma$ is a constant ranging between [0,1] and where the adaptive gain control is a value that corresponds to the adaptive gain control 232 of FIG. 2. Likewise, the microphone gain threshold could be calculated as follows:

$$\text{microphone gain threshold} = 1 - (\eta * \text{noise sensitivity control}) \quad (3)$$

where $\eta$ is a constant ranging between [0,1] and where the noise sensitivity control is a value generated by the noise sensitivity controller 224 described above. The noise sensitivity control can vary in value (see also FIGS. 5 and 6), causing the microphone gain threshold to also vary in some embodiments.

If the conditions at decision block 410 are satisfied, the environmental noise energy is provided to multiplication block 412. Otherwise, a low gain level can be provided to the multiplication block 412. The low gain level can be a minimum gain level or the like. The low gain level can be used, for example, in situations where the environmental noise energy is relatively low and where the voice input is relatively high. In these situations, little gain adjustment might be desired because the voice signal may already be relatively intelligible.

At multiplication block 412, the output of the decision block 410 is multiplied by the multiplicative inverse of the microphone gain threshold to produce a gain level. Alternatively, the output of the decision block 410 can be divided by the microphone gain threshold. Thus, the gain level can be a ratio of the environmental noise energy to the microphone gain threshold. At block 414, it is determined whether a high gain level has been reached. If not, the output of the multiplication block 412 is passed on to an output gain smoothing filter 416. Otherwise, a high gain level is provided to the output gain smoothing filter. The high gain level can be a maximum gain level or the like.

The output gain smoothing filter is applied at block 416 to the output of the decision block 414. The output gain smoothing filter can be a low pass filter or the like that averages out the gain level calculated at multiplication block 412 and/or decision block 414. This smoothing filter can reduce abrupt changes in the gain level. The output of the gain smoothing filter is multiplied by an output gain control at block 418, which can be a user set value. The output gain control can be exposed to a user via a user interface, for example. The output of the multiplication block 418 is provided as an output gain level at block 420.

V. Noise Sensitivity Control

As described above, the noise sensitivity control generated by the noise sensitivity controller 224 can be varied automatically or under user control. Varying the noise sensitivity control in certain embodiments influences the sensitivity of the voice enhancement controller 222 and/or the output gain controller 230 to noise. In one embodiment, increasing the noise sensitivity control causes the voice enhancement controller 222 to respond more aggressively to environmental noise by more aggressively enhancing voice intelligibility, and vice versa. Similarly, increasing the noise sensitivity control can cause the output gain controller 230 to more aggressively increase an output gain applied to an enhanced audio signal, and vice versa.

Automatically decreasing the sensitivity of the voice enhancement controller 222 and/or the output gain controller 230 can be beneficial in several situations. For instance, if the receiving phone 108 of FIG. 1 is merely receiving noise instead of a voice signal from the caller phone 104 (e.g., due to a pause in the conversation), applying the voice enhancement might increase the loudness of the noise. In addition, unpleasant effects can occur when the microphone of the receiving phone 108 is picking up the voice signal from the speaker output 114 of the phone 108. This speaker feedback can be interpreted as environmental noise by the voice enhancement controller 222, which can cause the voice enhancement to modulate the speaker feedback. The resulting modulated output signal 114 can be unpleasant to a listener. A similar problem can occur when the listener talks into the receiver phone 108 at the same time that the receiver phone 108 is outputting a voice signal received from the caller phone 104. The microphone of the receiving phone 108 can detect the double talk, and the voice enhancement controller 222 can cause the voice enhancement to modulate the double talk, resulting in an unpleasant sound.

Figure 5A:
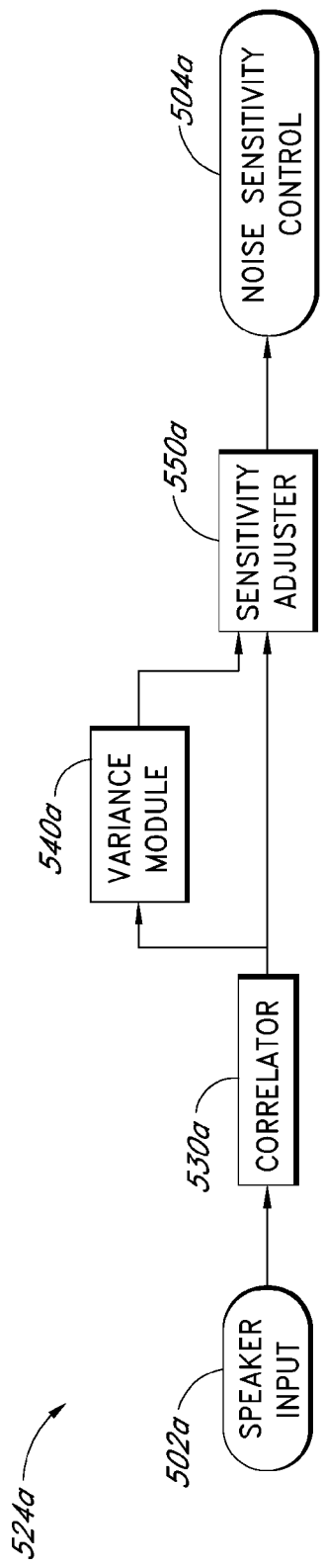
FIGS. 5A, 5B, 5C, and 6 illustrate embodiments of noise sensitivity control processes used by the voice enhancement system.
Figure 5B:
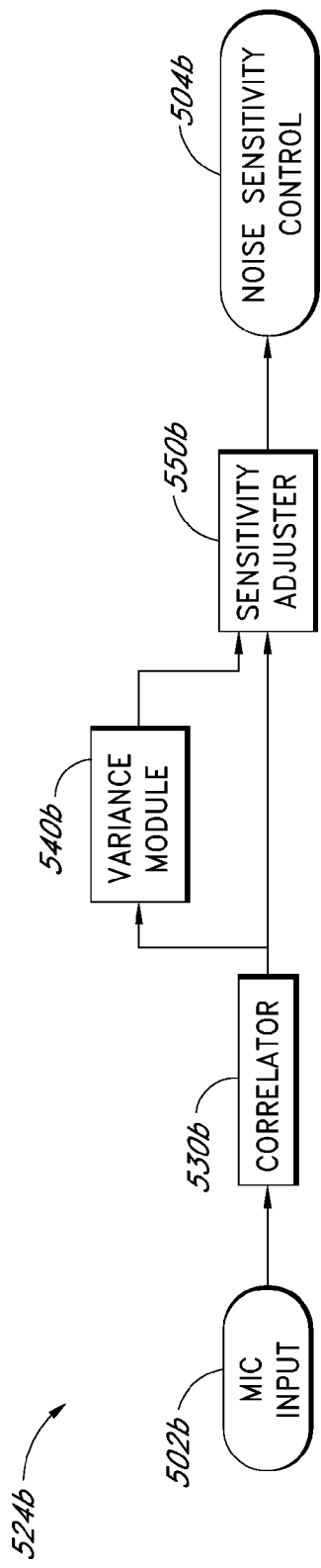
Figure 5C:
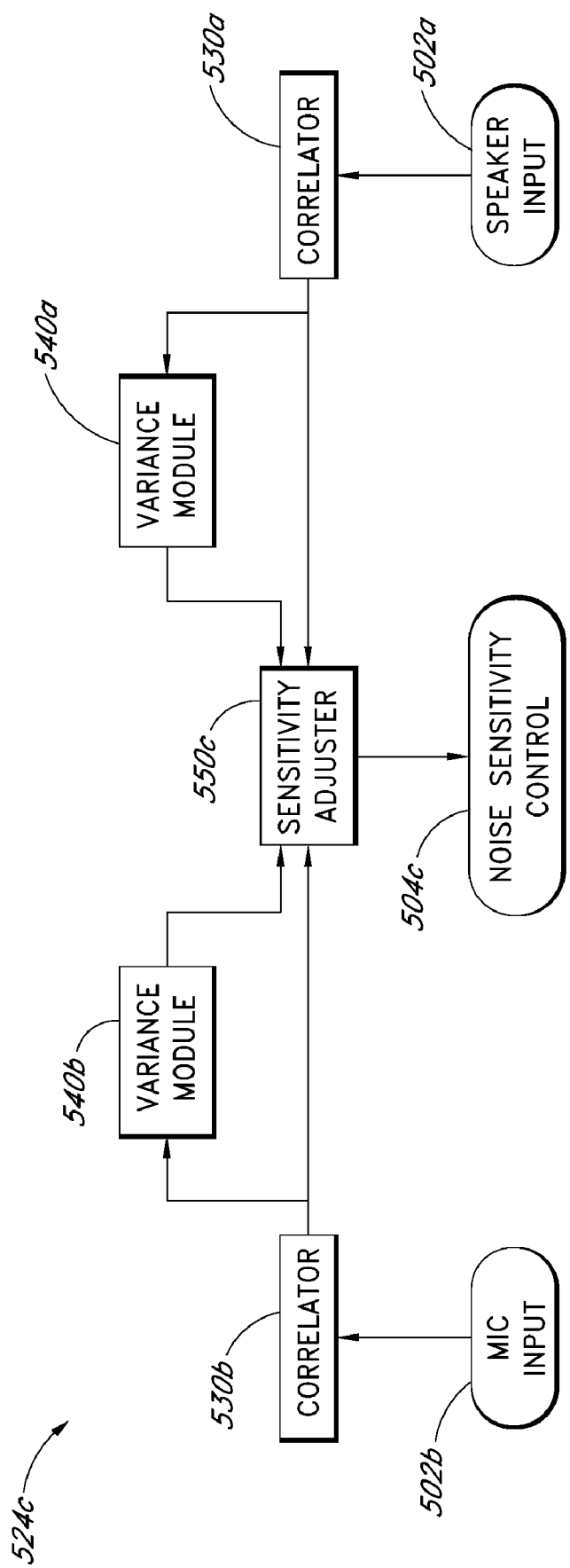
Figure 6:
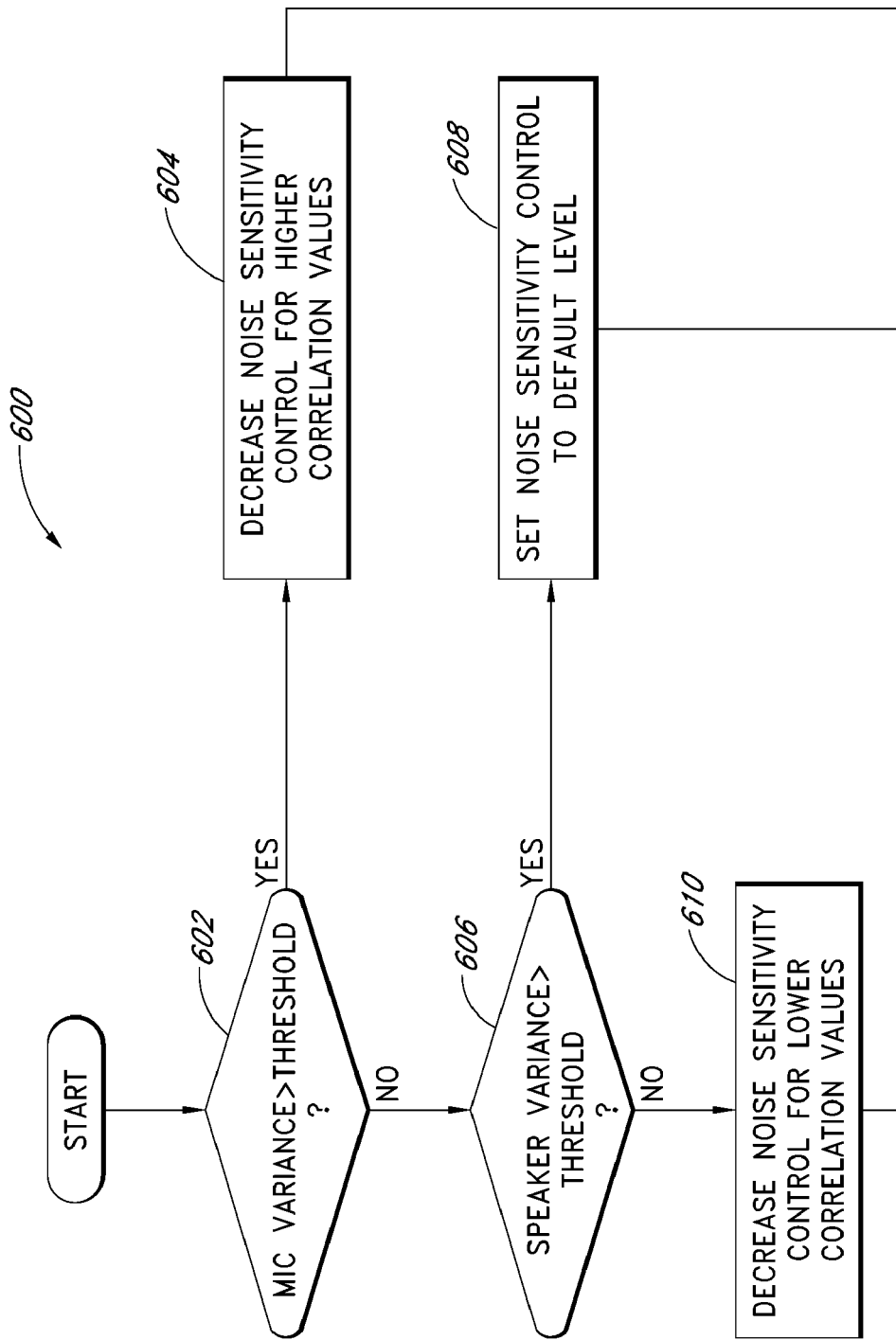

In certain embodiments, the noise sensitivity controller 224 can combat these and other issues by automatically adjusting the sensitivity of the voice enhancement controller 222 and/or the output gain controller 230 to noise. Alternatively, the noise sensitivity controllers 224 can toggle (e.g., turn on or turn off) the voice enhancement controller 222 and/or the output gain controller 230. Referring to FIGS. 5A, 5B, and 5C, more detailed embodiments of noise sensitivity controllers 524a, 524b, and 524c are shown. The noise sensitivity controller 524a of FIG. 5A can adjust noise sensitivity of the controllers 222, 230 or toggle the controllers 222, 230 to account for situations where the receiving phone 108 is merely receiving noise instead of a voice signal from the far end (e.g., from the caller phone 104). The noise sensitivity controller 524a of FIG. 5B can adjust noise sensitivity of the controllers 222, 230 or toggle the controllers 222, 230 to account for speaker feedback and/or double talk situations. The noise sensitivity controller 524c of FIG. 5C combines the features of the controllers 524a, 524b shown in FIGS. 5A and 5B.

In FIG. 5A, the noise sensitivity controller 524a receives a speaker input 502a. The speaker input 502a can include one or more output samples stored in a buffer or the like, which are also provided to a speaker of a communication device such as the phone 108. The speaker input 502a could be the output signal 250 of the voice enhancement system 210 described above. The speaker input 502a is provided to a correlator 530a, which can calculate or estimate the autocorrelation of the speaker input 502a. In an embodiment, the correlator 530a calculates the autocorrelation of a block of samples in the speaker input 502a.

Voice signals tend to be periodic or substantially periodic. Thus, if the speaker input 502a includes a voice signal, due to the properties of autocorrelation, an autocorrelation function of the speaker input 502a can also be periodic or substantially periodic. Noise signals, on the other hand, are often uncorrelated and not periodic (some exceptions are described below). Evaluation of an autocorrelation of a periodic or substantially periodic signal can result in a greater value than the autocorrelation of many noise signals.

The autocorrelation value calculated by the correlator 530a is provided to a sensitivity adjuster 550a. In one embodiment, if the autocorrelation is low or below a threshold, the speaker input 502a is most likely noise. Thus, the sensitivity adjuster 550a can reduce a noise sensitivity control 504a corresponding to the noise sensitivity control of equations (1) and (3) above. Adjusting the noise sensitivity control 504a can therefore adjust the noise threshold used by the voice enhancement controller 222 and/or the mic gain threshold used by the output gain controller 230. As a result, the voice enhancement controller 222 and/or output gain controller 230 can respond less aggressively to environmental noise. If the autocorrelation is high or above a threshold (representing a speaker input 502a that likely includes voice), the sensitivity adjuster 550a can increase the noise sensitivity control 504a. As a result, the voice enhancement controller 222 and/or output gain controller 230 can respond more aggressively to environmental noise.

In certain embodiments, the amount of sensitivity adjustment provided by the sensitivity adjuster 550a can correspond to the autocorrelation level. For example, the lower the autocorrelation, the lower the sensitivity adjuster 550a might make the noise sensitivity control 504a, and vice versa.

In the depicted embodiment, the correlator 530a also provides autocorrelation values to an optional variance module 540a. The variance module 540a can calculate or estimate the variance of a block of autocorrelation values. The variance module 540a can provide the resulting variance values to the sensitivity adjuster 550a, which can use the variance values to refine the adjustment of the noise sensitivity control 504a. Higher variance values can reflect the presence of a voice signal, whereas lower variance values can reflect the presence of primarily noise. Thus, the sensitivity adjuster 550a can include logic to increase the noise sensitivity control 504a when both the autocorrelation and the variance values are high and can decrease the noise sensitivity control 504b when one or both values are low.

Many alternative configurations for the example noise sensitivity controller 524a shown may be provided. For example, the variance module 540a may be omitted. Alternatively, the correlator 530a can provide values only to the variance module 540a, and the sensitivity adjuster 550a can adjust the noise sensitivity control 504a based solely on the variance values. In addition, the correlator 530a can use other statistical measures to analyze the speaker input 502a. For example, the correlator 530a could use any normalized unbiased estimator. In one embodiment, the correlator 530a normalizes the correlation by the total power or energy in a block of samples. Normalizing the correlation by the power can cause the sensitivity adjuster 550a to adjust the noise sensitivity control 504a based on characteristics of the input signal 502a rather than on variations in the power of the input signal 502a.

Referring to FIG. 5B, the example noise sensitivity controller 524b includes many of the features of FIG. 5A. However, instead of receiving a speaker input 502a, the noise sensitivity controller 524b receives a microphone ("mic") input 502b, which can include a block of samples received by a microphone. Applying the correlation and/or variance techniques described above to the mic input 502b can allow the noise sensitivity controller 524b to improve voice intelligibility processing in the presence of speaker feedback and/or double talk.

The mic input 502b is provided to a correlator 530b, which can provide the same autocorrelation features described above. In the case of speaker feedback or double talk, the mic input 502b might include periodic or substantially periodic information. As a result, the autocorrelation function can be periodic or substantially periodic, and the autocorrelation values computed by the correlator 530b can be higher than the autocorrelation of many forms of noise.

As before, the correlator 530b can provide autocorrelation values to a sensitivity adjuster 550b. If the autocorrelation values are high or above a threshold, the sensitivity adjuster 550b can reduce the noise sensitivity control 504b to reduce the voice enhancement modulation caused by speaker feedback and/or double talk. Similarly, if the autocorrelation values are low or below a threshold, the sensitivity adjuster 550b can increase the noise sensitivity control 504b. As above, the sensitivity adjuster 550b can adjust the amount of noise sensitivity control 504b based at least partly on the autocorrelation level.

The correlator 530b also provides autocorrelation values to an optional variance module 540b. The variance module 540b can calculate the variance or an approximation of the variance of a block of autocorrelation values. The variance module 540b can provide the resulting variance values to the sensitivity adjuster 550b, which can use the variance values to refine the adjustment of the noise sensitivity control 504b. Higher variance values can reflect the presence of speech feedback and/or double talk, whereas lower variance values can primarily reflect the presence of noise. Thus, the sensitivity adjuster 550b can also decrease the noise sensitivity control 504a when the variance is high and vice versa.

The variance module 540b can beneficially account for certain noise signals that have harmonic content. Some noise signals, such as those generated by autos and planes, have low frequency harmonic content that can result in higher correlation values. However, the autocorrelation of these noise signals may have lower variance values than for voice signals. Thus, the sensitivity adjuster 550b might include logic to decrease the noise sensitivity control 504b when both the autocorrelation and variance values are high and increase the noise sensitivity control 504b when one or both values are low.

The alternative configurations described above with respect to the noise sensitivity controller 524a can also be applied to modify the noise sensitivity controller 524b in various embodiments. Moreover, in alternative embodiments, an acoustic echo canceller could be used in place of (or in addition to) the correlator 530b, the variance module 540b, and/or the sensitivity adjuster 550b. The acoustic echo canceller could reduce or cancel echo received from a speaker at the mic input 502b. Any suitable acoustic echo canceller could be used. For example, an acoustic echo canceller could be employed that implements features described in the ITU-T Recommendation G.167 of March 1993, which is hereby incorporated by reference in its entirety. However, the correlation and/or variance features described herein can advantageously be implemented in certain embodiments with fewer processing resources than an acoustic echo canceller.

Referring to FIG. 5C, the noise sensitivity controller 524c combines the features of the noise sensitivity controllers 524a and 524b. Specifically, the noise sensitivity controller 524c receives both the mic input 502b and the speaker input 504a. The speaker input 502a is provided to the correlator 530a, which provides autocorrelation values to a sensitivity adjuster 550c, and to the variance module 540a, which provides variance values to the sensitivity adjuster 550c. The mic input 502b is provided to the correlator 530b, which provides autocorrelation values to the sensitivity adjuster 550c, and to the variance module 540b, which provides variance values to the sensitivity adjuster 550c.

The sensitivity adjuster 550c can include logic to adjust a noise sensitivity control 504c based at least in part on information received from any of the components 530a, 530b, 540a, and 540b. In certain embodiments, the sensitivity adjuster 550c performs a soft decision to adjust the noise sensitivity control 504c. One example of a process 600 that can be performed by the sensitivity adjuster 550c is depicted by in FIG. 6. At decision block 602 of the process 600, it is determined whether a mic variance value is greater than a threshold. The mic variance value can be calculated by the variance module 540b. If the variance in the autocorrelation of the mic input 502b is greater than the threshold, there may be a periodic or substantially periodic signal present due to speech feedback or double talk. Thus, at block 604, the sensitivity adjuster 550c decreases the noise sensitivity control based at least in part on correlation values from the correlator 530b, with higher correlation values potentially resulting in a bigger decrease.

If the mic variance is less than the threshold, it is determined at decision block 606 whether a speaker variance is less than a threshold. The speaker variance value can be calculated by the variance module 540a from the autocorrelation of the speaker input 502a. If the speaker variance is above a threshold, then a speech signal is likely present in the speaker input 502a. Thus, the sensitivity adjuster 550c sets the noise sensitivity control to a default level at block 608.

If the speaker variance is below a threshold, then noise is likely present in the speaker input 502a. Thus, the sensitivity adjuster 550c decreases the noise sensitivity control based at least in part on correlation values from the correlator 530a, with lower correlation values potentially resulting in a bigger decrease.

The process 600 illustrates one example implementation of the sensitivity adjuster 550c. In other embodiments, hysteresis may be provided to one or both of the thresholds described in the process 600. In still other embodiments, the noise sensitivity control is set to a certain low value in block 604 that does not depend directly on correlation values. Likewise, the noise sensitivity control in block 610 could be set to a value that does not depend on correlation values. In addition, other statistical measures than autocorrelation and variance may be used to adjust noise sensitivity, including standard deviation, higher order moments, acoustic echo cancellation, and the like. Many other configurations are also possible.

More generally, any of the noise sensitivity controllers described above can be considered to be voice, dialog, or speech classifiers that detect and/or classify one or more voice, dialog, or speech components of an input audio signal. The noise sensitivity controllers can also be considered to be voice detectors or general signal classifiers. The noise sensitivity controllers can perform voice or signal classification or detection at least in part by using one or more processors to analyze one or more statistics of an input audio signal. Autocorrelation and variance, acoustic echo cancellation, and estimators are mere examples of techniques that can be employed by the noise sensitivity controllers. Other techniques, including other statistical techniques, can be used to detect voice or other components of an input signal.

In addition, speech feedback and double talk are also mere examples of voice components that can be detected. The features of the noise sensitivity controllers described above with respect to FIGS. 5 and 6 can be used to detect other voice components in audio signals, including voice components in any media content, such as television, radio, music, and other content. A controller could, for example, detect a voice component in media content using an autocorrelation of audio in the media content. In one embodiment, the controller could provide the detected voice component to a dialog enhancement, increasing or decreasing the amount of dialog enhancement applied and thereby enabling the dialog enhancement to more effectively enhance dialog.

VI. Distortion Control

The voice enhancement controller 222 and/or the output gain controller 230 can increase one or more gains applied to a voice signal. In some cases, increasing the gains beyond a certain point can result in saturation of the signal, which can create distortion. Advantageously, in certain embodiments, the distortion control module 240 described above can provide controlled distortion, and hence greater loudness.

Figure 7:
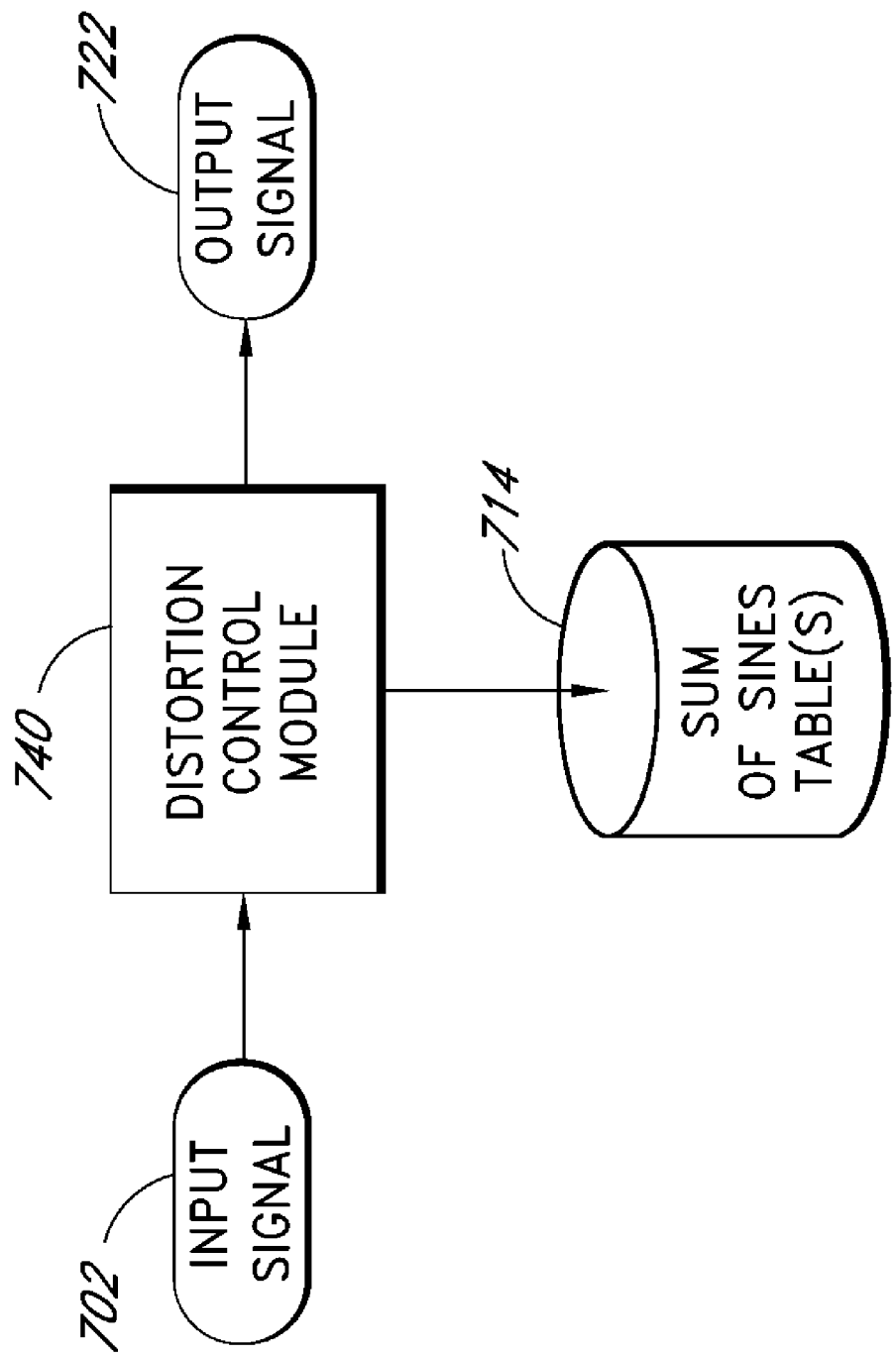
FIG. 7 illustrates an example distortion control module of the system of FIG. 1.

FIG. 7 illustrates a more detailed embodiment of a distortion control module 740, which can have all of the features of the distortion control module 140 described above. The distortion control module 740 can be implemented in hardware and/or software. In certain embodiments, the distortion control module 740 can induce selected distortion in the audio signal to increase signal energy and hence loudness. This selected distortion can be a controlled distortion that adds fewer harmonics than are present in fully-saturated signals.

As described above, the distortion control module 740 can induce selected distortion at least in part by mapping input samples into output samples. The distortion control module 740 can perform this mapping by using samples of the input signal 702 as indices into a sum-of-sines table 714 or tables. The sum-of-sines table 714 can include values that are generated by summing harmonically-related sine waves.

To illustrate, if the input signal 702 has a sample with a value m, the distortion control module 740 can map the input sample to an output sample at an index m in the sum-of-sines table 714. If the sample of the input signal 702 falls between index values of the table 714, the distortion control module 740 can interpolate an index value. Using interpolation can allow the size of the sum-of-sines table 714 to be reduced in order to save memory. However, the sum-of-sines table 714 can be designed to be large enough so as to avoid the use of interpolation in certain embodiments. The distortion control module 740 can use the mapped output value of the sum-of-sines table 714 as an output sample for the output signal 722.

The sum-of-sines table 714 can be implemented as any data structure, such as an array, matrix, or the like. The table 714 can be generated to include an arbitrary number of harmonic sine waves, including odd harmonics, even harmonics, or a combination of both. In certain embodiments, odd harmonics provide good distortion control for voice audio signals. Even harmonics can be used in other implementations and can be good for reducing clipping in music signals. Either odd or even harmonics can be used for mixed voice and music signals. However, these are merely illustrative examples, and either odd or even harmonics or both could be used for any application.

When more sine waves are used to generate the table 714, the potential increase in signal energy and distortion is greater, and vice versa. As using a large number of sine waves could result in significant harmonic distortion, in certain embodiments, a relatively small number of lower-frequency sine waves are beneficially used to construct the sum-of-sines table 714.

For instance, the table 714 can be constructed from the sum of two or three harmonically-related sine waves, four sine waves, five sine waves, or more. Multiple sum-of-sines tables 714 can be stored in a memory and can be used by the distortion control module 740 for different purposes. For example, a sum-of-sines table 714 with more harmonics might be used for voice signals while a table 714 with fewer harmonics might be used for music to create less distortion.

The distortion control module 740 can also provide a user interface that provides a distortion control for a user to adjust the amount of signal energy increase and/or distortion. For example, a graphical slider, knob, or the like can be provided, or the user can be able to press a physical or soft button to adjust the amount of energy increase or distortion applied. Increasing the distortion control could cause a table with more harmonics to be used, and vice versa.

An example process for generating a sum-of-sines table 714 will now be described, using three odd-harmonically related sine waves. In this example, the sum-of-sines table 714 can be generated by populating a first table of a selected size with values of one period of a sine wave (e.g., from 0 radians to 2 pi). Populating a table of size N (N being an integer) can include dividing one period of the sine wave into N values and assigning the N values to the N slots in the table. This first sine wave table can represent the fundamental or first harmonic.

A second table of the same size as the first table can be populated with three periods of a sine wave in a similar fashion, by dividing the three sine periods into N values. The values in the second table can represent the third harmonic of the first sine wave. Similarly, a third table of the same size as the first two can be populated with five periods of a sine wave, representing the fifth harmonic. The values in the first, second, and third tables can be scaled as desired. For instance, the values in the second table can be scaled lower to be lower in magnitude than those in the first table, and values in the third table can be scaled to include lower values than the second table.

Because the three tables are the same size in certain embodiments (e.g., have the same number of N entries), the values in corresponding indices of the three tables can be added together to create a new sum-of-sines table 714 that includes the sum of the first, third, and fifth harmonics. Thus, if one were to plot the values in the sum-of-sines table 714, in certain embodiments, an approximation of one period of the summed waves would be shown. The more sine waves that are used, in certain embodiments, the closer this plotted wave would look like a square wave. In various embodiments, other sum-of-sines tables with different harmonics can be constructed in a similar fashion to that described for three odd harmonics. Alternatively, portions of sine wave periods can be used, rather than full periods, to construct the sum-of-sines table 714.

As the distortion control module 740 maps samples from the input 702 signal into the sum-of-sines table 714, the frequency of the harmonics in the table 714 can depend on the table lookup rate, which in turn can depend on the frequency of the input signal. This frequency dependence results in certain embodiments from the table-lookup operation being performed by the distortion control module 740 at or near the same rate as the frequency of the input signal 702.

To illustrate, for a simple sine wave input signal 702 having a given frequency, the distortion control module 740 could perform the mapping operation at the same frequency. The resulting harmonics would have particular frequencies that depend on the frequency of the sine wave. Doubling the frequency of the sine wave could therefore double the frequency of the harmonics. For input signals 702 that include multiple frequencies superimposed, the mapping by the distortion control module 740 could result in a superposition of harmonics.

Figure 8:
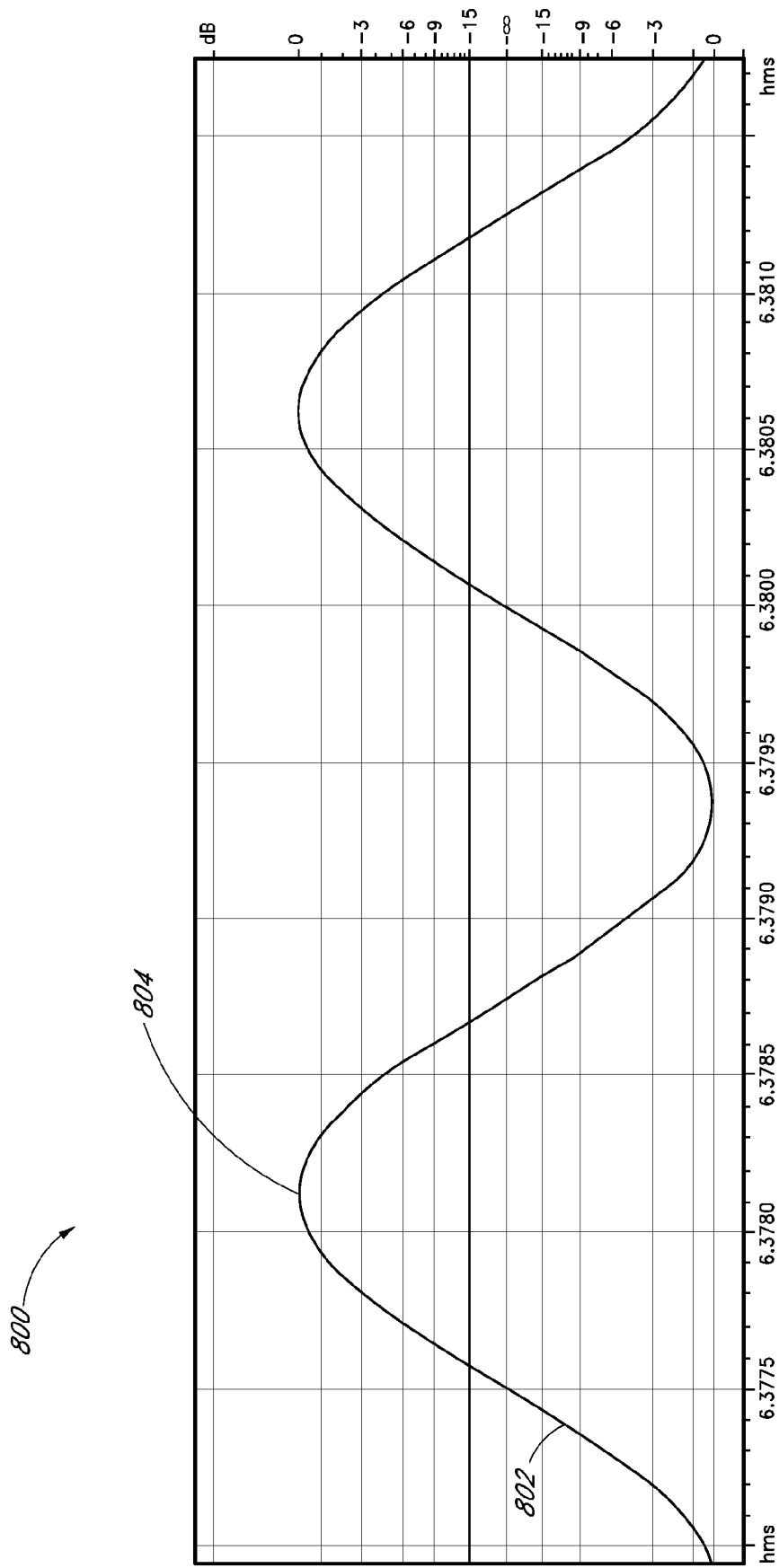
FIG. 8 illustrates an example time domain representation of a sine wave.
Figure 9:
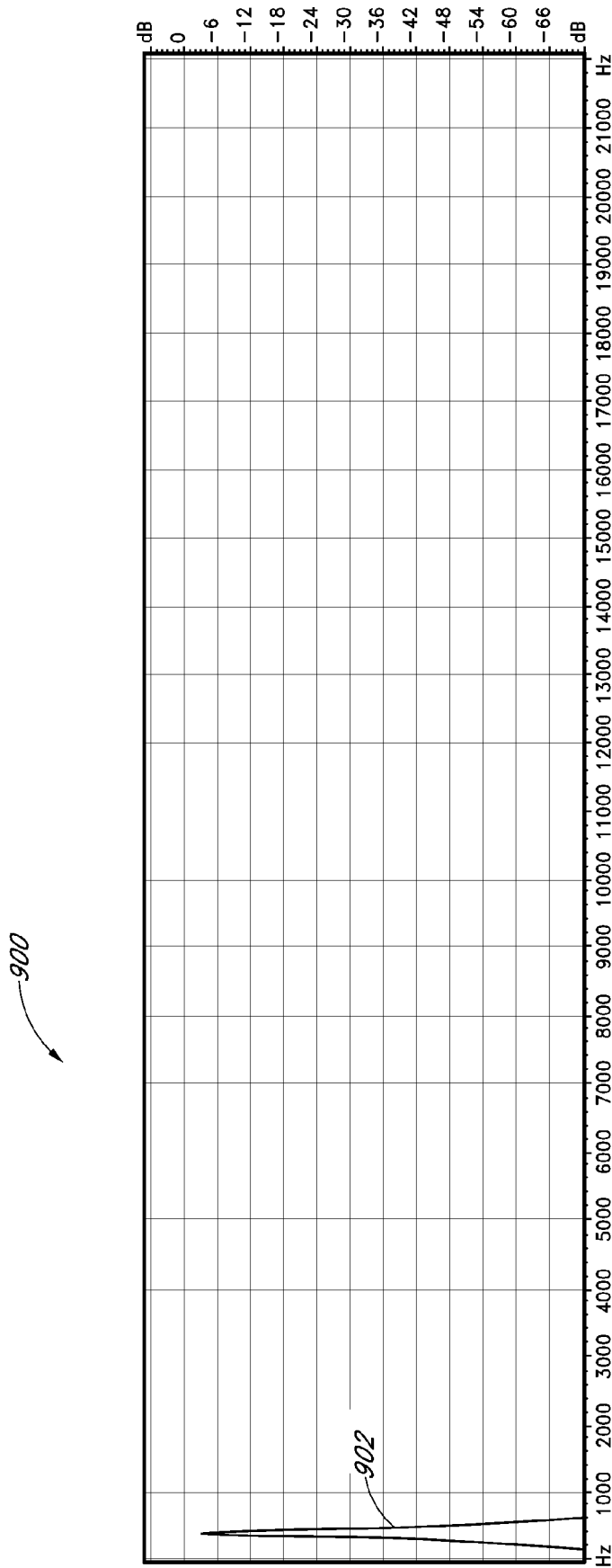
FIG. 9 illustrates an example frequency spectrum of the sine wave of FIG. 8.
Figure 10:
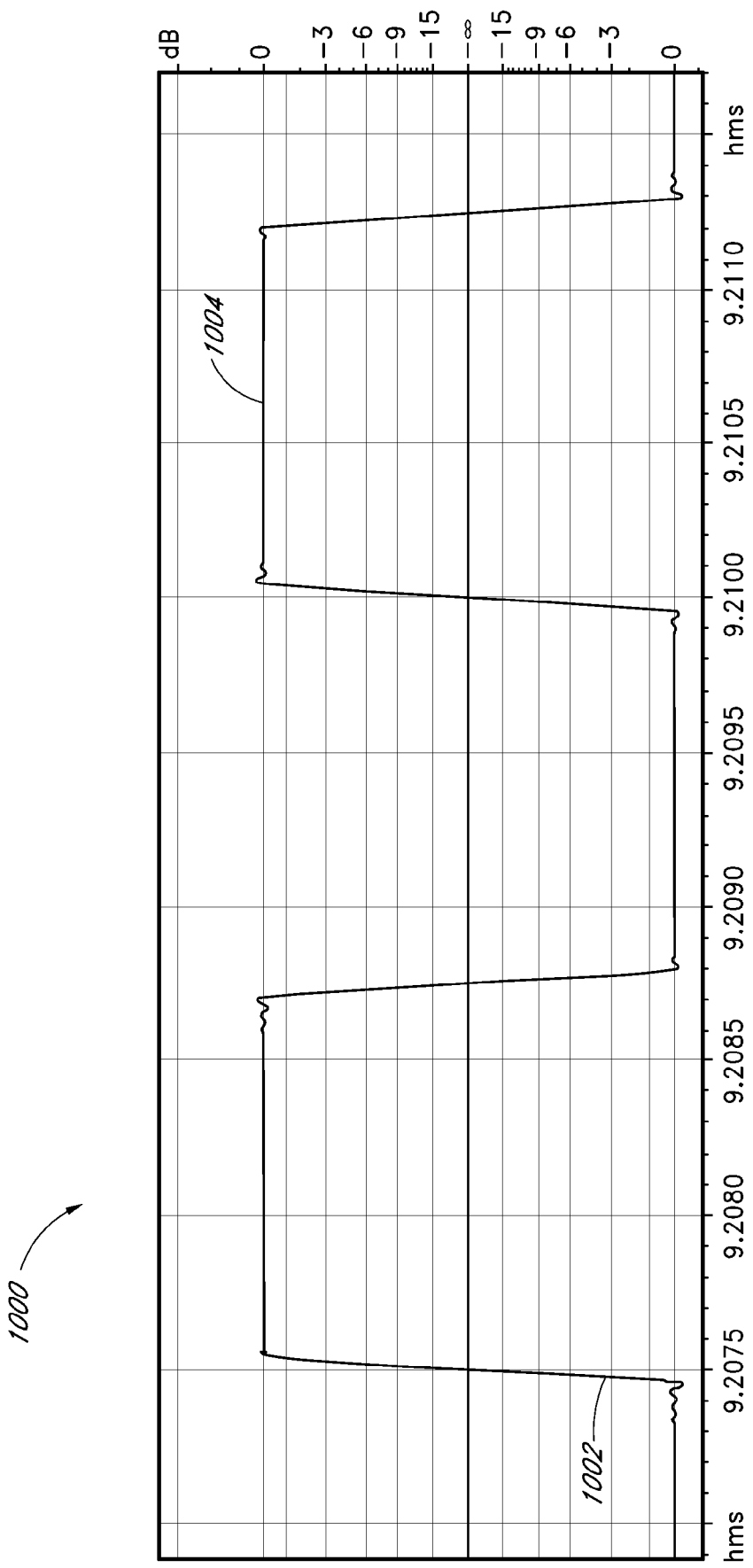
FIG. 10 illustrates an example time domain representation of a clipped sine wave.
Figure 11:
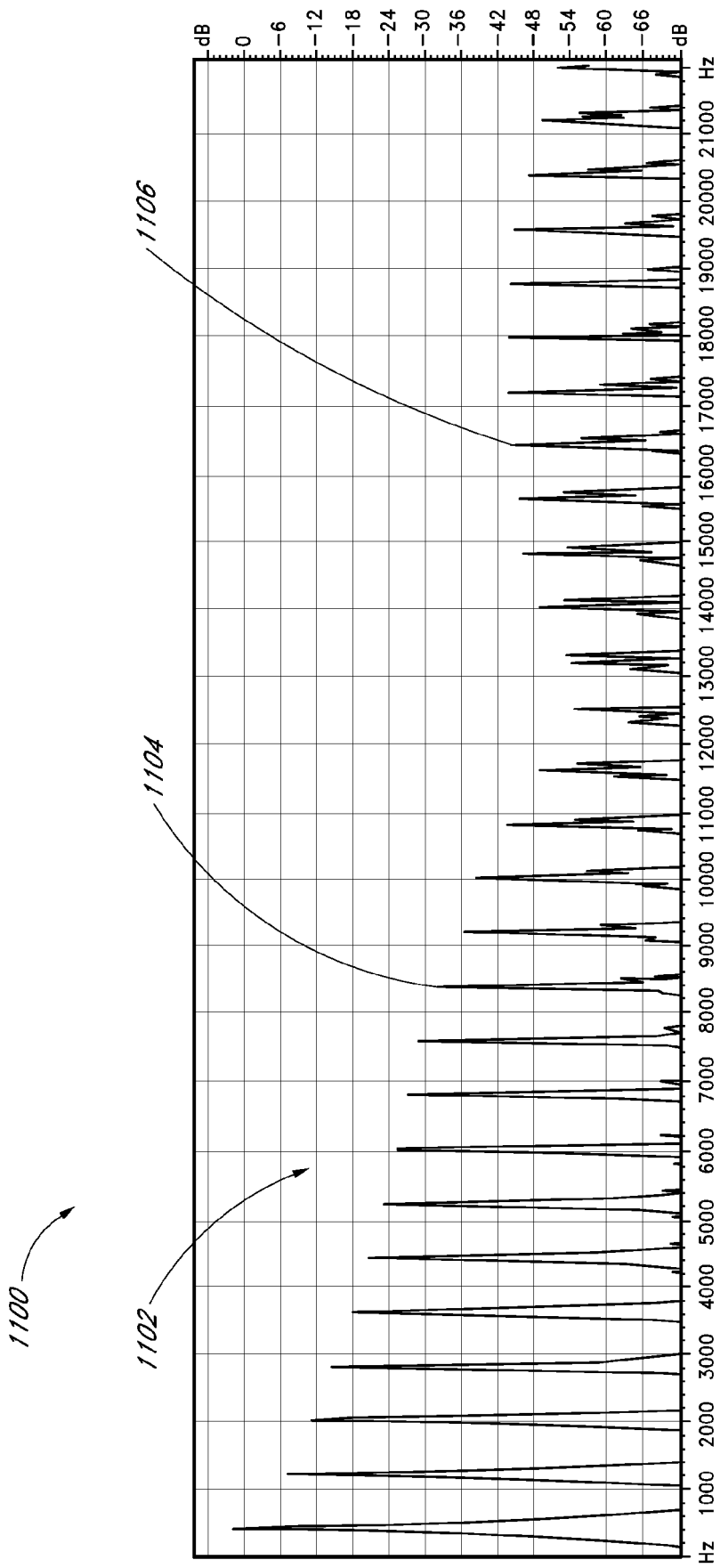
FIG. 11 illustrates an example frequency spectrum of the clipped sine wave of FIG. 10.

FIGS. 8 through 15 illustrate examples of distortion and sum of sines waves. For reference, FIG. 8 illustrates an example time domain plot 800 of a sine wave 802. A peak level 804 of the sine wave 802 without clipping is shown. The peak level 804 of the sine wave 802 is at 0 db, which can be a peak possible digital level in some embodiments. FIG. 9 illustrates an example plot 900 showing a frequency spectrum 902 of the sine wave 802 of FIG. 8. As it is a sinusoid, one frequency is represented.

In certain embodiments, increasing the amplitude of the sine wave 802 beyond the peak level can result in hard clipping. Hard clipping of a sinusoid 1002 is shown in a plot 1000 of FIG. 10. The clipped sinusoid 1002 includes clipped portions 1004, which are saturated at the peak level. Examples of harmonics 1104 of the clipped sine wave 1002 can be seen in the frequency domain representation 1102 shown in FIG. 11. As shown, the harmonics 1104 can extend as high as the sampling frequency (about 22 kHz in the example FIGURE shown). Certain of the harmonics 1106 are also aliased, causing further distortion.

Figure 12:
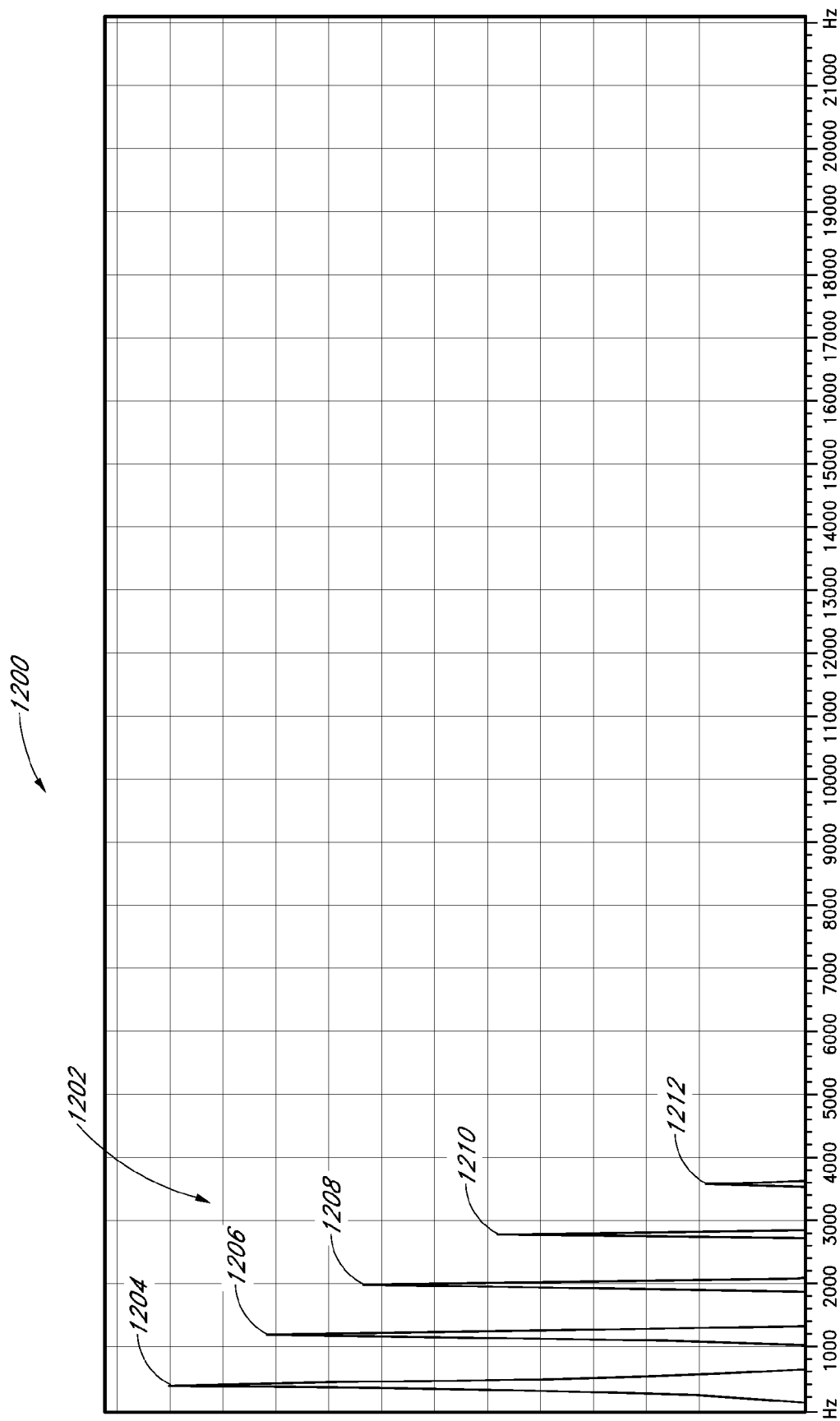
FIG. 12 illustrates an example frequency spectrum having a reduced number of harmonics compared to the clipped sine wave spectrum of FIG. 11.

To avoid the full distortion of hard clipping while still allowing an increase in volume, the distortion control module 740 can use a composite wave of lower-frequency harmonics, as described above. An example set of harmonics of such a wave is illustrated in FIG. 12, which includes an example frequency response plot 1200 of a composite wave that can be generated in response to a 400 Hz input sine wave. The spectrum in the plot 1200 includes fewer harmonics 1202 than in the full clipping scenario of FIG. 11. In the depicted embodiment, five harmonics 1202 have been generated. The highest harmonic 1202 is at a lower frequency than the high frequency harmonics 1104 of FIG. 11. Aliased harmonics 1106 are also not present in this embodiment.

The example embodiment shown includes harmonics 1202 at about 400 Hz, 1200 Hz, 2000 Hz, 2800 Hz, and 3600 Hz. These harmonics 1202 are odd harmonics 1202, which include the first 1204, third 1206, fifth 1208, seventh 1210, and ninth harmonic 1212. The first harmonic 1204 has an amplitude of about 0 dB, which in certain embodiments, is a highest possible digital amplitude. Successive harmonics 1202 have lower amplitudes as the frequency increases. In an embodiment, the amplitude of the harmonics 1202 decreases monotonically. These amplitudes can vary in other embodiments.

Figure 13:
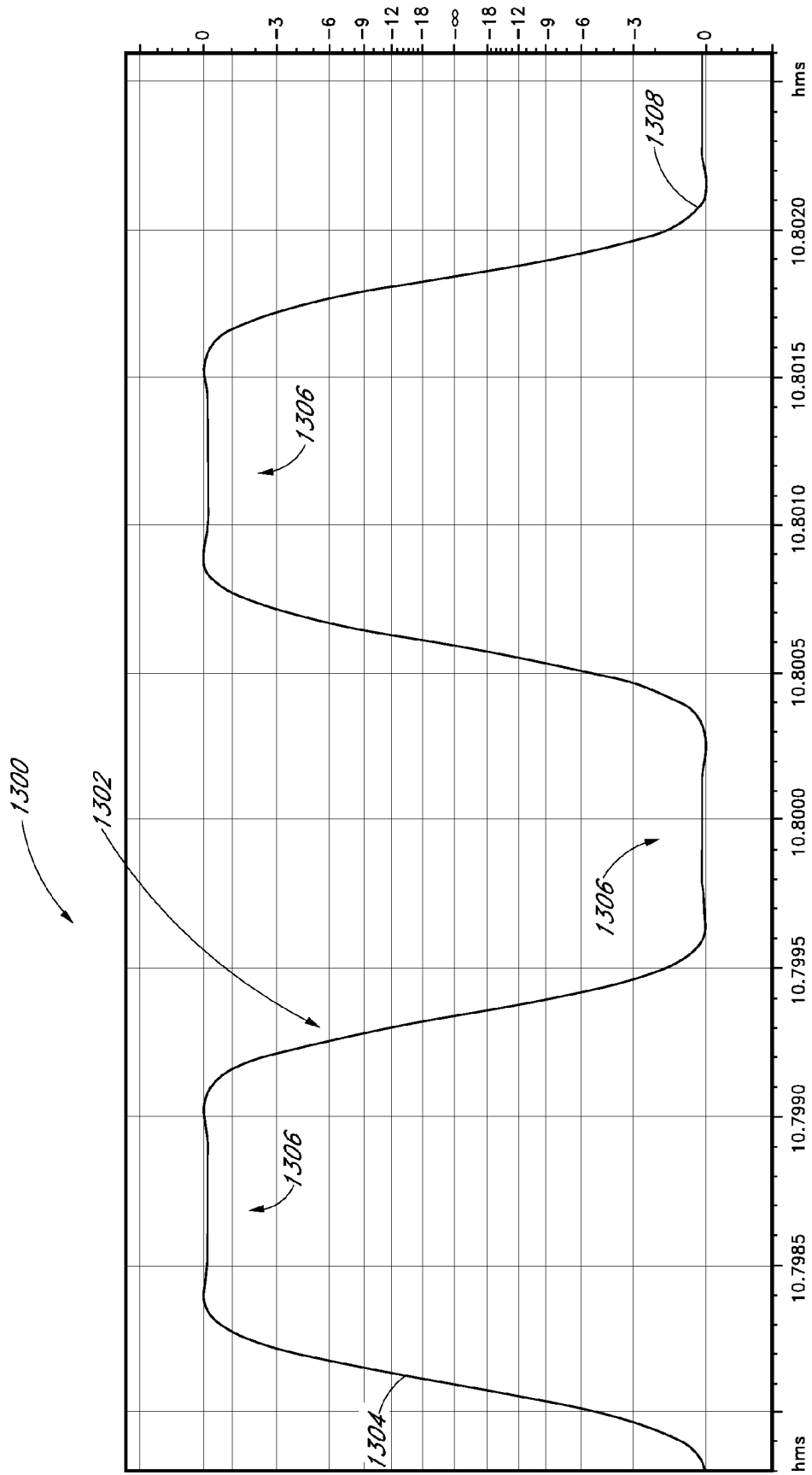
FIG. 13 illustrates an example time domain representation of a partially saturated wave corresponding to the spectrum of FIG. 12.

The result of the controlled distortion provided by lower frequency harmonics can be a rounded and more natural sounding waveform with a higher signal energy or higher average signal energy. An example time domain plot 1300 of a wave 1302 illustrating a sine wave mapped to the harmonics 1204 of FIG. 12 is shown in FIG. 13. The example wave 1302 shown has partially clipped portions 1306 and rounded portions 1308. Comparison between the wave 1302 and the hard clipped wave 1002 shows that the wave 1302 is more rounded than the hard clipped wave 1002. In addition, portions 1304 of the wave 1302 are linear or approximately linear. The curved portions 1308 begin curving at about −3 dB from the clipped portions 1306.

Figure 14:
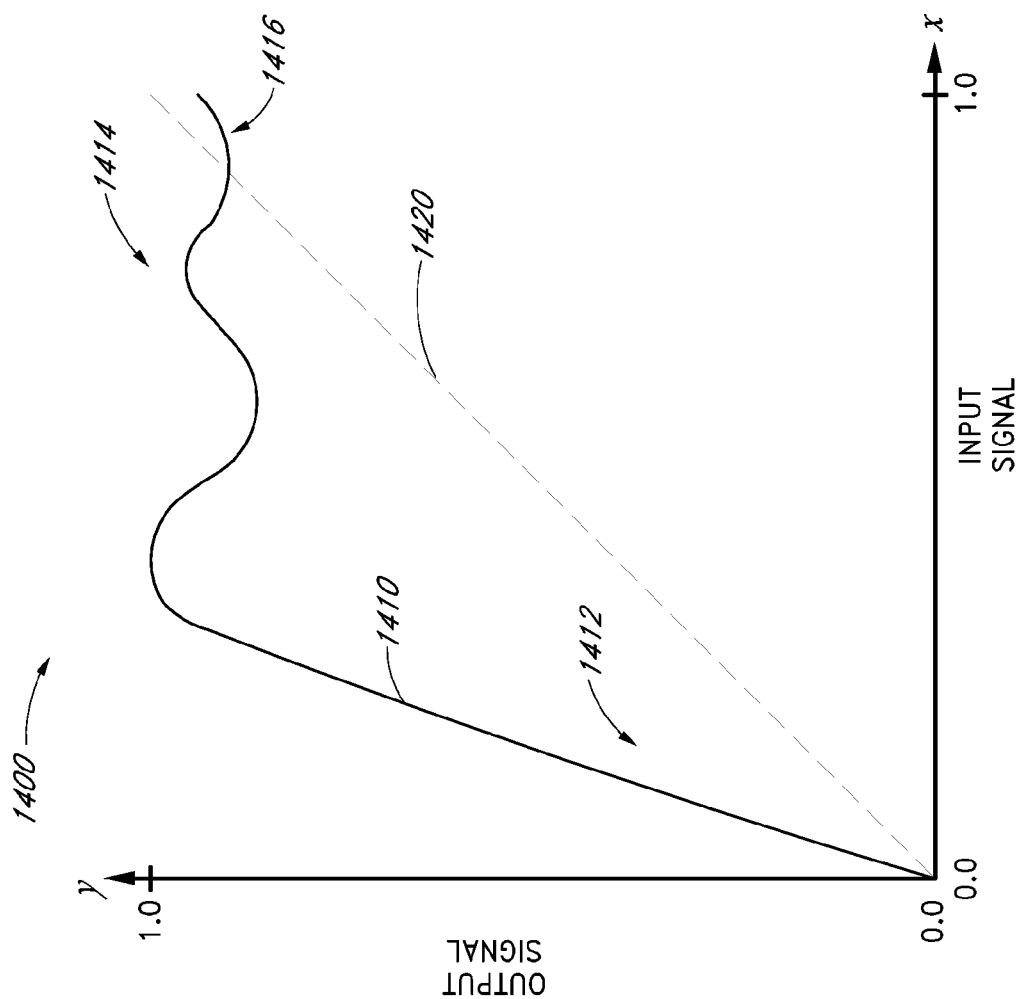
FIG. 14 illustrates an embodiment of a sum-of-sines mapping function.

FIG. 14 illustrates an example plot 1400 that depicts an embodiment of a sum-of-sines mapping function 1410. The sum-of-sines mapping function 1410 shown can be plotted by plotting values in a sum-of-sines table, such as the table 714 described above. The sum-of-sines mapping function 1410 includes one quarter of a period of a sum-of-sines wave. One quarter of a sum-of-sines wave can be used instead of a full wave for an optimization, which will be described below.

Input signal values are depicted on the x-axis, which include positive amplitude values ranging from 0 to 1. Similarly, output signal values are depicted on the y-axis and also include amplitude values ranging from 0 to 1. Negative amplitude values will be described below. When the distortion control module 140 or 740 maps an input sample to an output sample, in certain embodiments the input sample is mapped to a point on the mapping function 1410. The mapped output sample can have a greater or lower value than the input sample, depending on where the input sample is mapped.

For clarity, the sum-of-sines mapping function 1410 is shown as a continuous function. However, when implemented in a digital system, the mapping function 1410 can be discrete. In addition, as described above, the mapping function 1410 cannot be defined for all input signal values. Thus, the distortion control module 140 or 740 can interpolate output signal values, for example, between the two nearest points on the mapping function 1410.

A phantom line 1420 is shown for reference, which corresponds to the line y=x. If input samples were to be mapped according to the phantom line 1420, the output samples would be the same as the input samples. The mapping function 1410 includes a linear or approximately linear mapping region 1412 and a nonlinear or approximately nonlinear mapping region 1414. As input sample values falling in the linear mapping region 1412 increase in value, the corresponding output samples in the linear mapping region 1412 increase linearly or substantially linearly. Certain input sample values falling in the nonlinear region 1414 increase nonlinearly or substantially nonlinearly, having varying levels of increase 1414.

Most values of the mapping function 1410 are greater than the phantom line 1420, such that most input samples can be mapped to greater values. However, in region 1416 of the nonlinear mapping region 1414, the values of the mapping function 1410 are less than or equal to the phantom line 1420. In this region 1416, input samples are mapped to lower values. Thus, for example, hard-clipped samples (e.g., having a value of 1.0 or close to 1.0) can be reduced in value.

As mentioned above, the mapping function 1410 includes one quarter of a sum-of-sines wave instead of a full wave.

Using a quarter wave (or even half wave) can enable the size of the sum-of-sines table 714 to be reduced, thereby saving memory. For negative input signal values (e.g., on a scale of 1-,0) or the like), the distortion control module 140, 740 can reverse the mapping function 1410 across the x-axis and invert the mapping function 1410 across the y-axis. Thereafter, the distortion control module 140, 740 can apply the mapping function 1410 to the input samples. Alternatively, negative values can be inverted and normalized to the [0, 1] range. Then the mapping function 1410 can be applied, and the resulting output samples can be negated to recover the negative values.

In alternative embodiments, the mapping function 1410 shown can look different depending, for example, on the number of harmonics used to generate the sum-of-sines table 714. For instance, the linear mapping region 1412 can have a greater or lesser slope. The nonlinear mapping region 1414 can be shaped differently; for example, it can have fewer peaks. Likewise, the region 1416 can be lower or greater in amplitude.

In certain embodiments, the ranges of the x and/or y axis can differ from the [0, 1] ranges described above. Decreasing the x-axis range to [0,a], where a is less than 1, can increase amplification of at least part of the input signal. Conversely, increasing the x-axis range from [0,b], where b is greater than 1, can decrease amplification of at least part of the input signal. Using a value of b that is greater than 1 can beneficially reduce clipping in some embodiments. Similarly, the y axis can be changed to [0,c], where c is less than or greater than 1.

Figure 15:
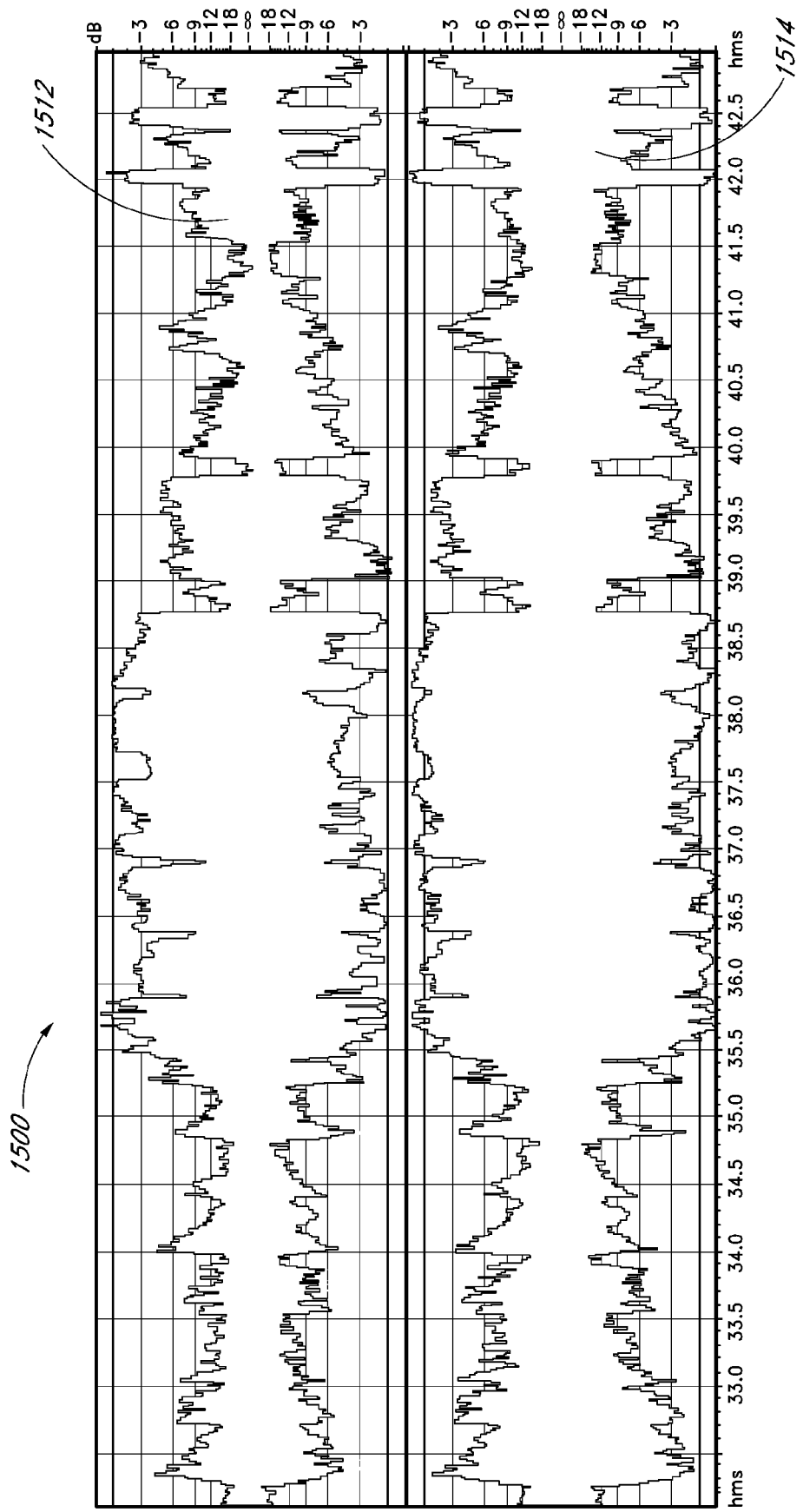
FIG. 15 illustrates an example time domain representation of an audio signal and a distortion controlled version of the signal.

FIG. 15 illustrates a plot 1500 of an example time domain representation of an audio signal 1512 before distortion control is applied. In addition, FIG. 15 shows an example time domain representation of the same audio signal 1514 after distortion control is applied. Approximately 6 dB of additional gain has been introduced into this waveform by using an example implementation of distortion control.

Distortion control can be used for other applications. For example, distortion control can be used to increase bass volume with reduced distortion. Distortion control can also be used in frequency spreading applications. Moreover, distortion control can be used to synthesize instrument sounds or other sounds, for example, by selecting various harmonics to create a desired timbre of an instrument.

VII. Conclusion

Depending on the embodiment, certain acts, events, or functions of any of the algorithms described herein can be performed in a different sequence, can be added, merged, or left out all together (e.g., not all described acts or events are necessary for the practice of the algorithm). Moreover, in certain embodiments, acts or events can be performed concurrently, e.g., through multi-threaded processing, interrupt processing, or multiple processors or processor cores, rather than sequentially.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a processor, controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of processor-readable or computer-readable storage medium known in the art. An exemplary storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A method of adjusting a voice intelligibility enhancement, the method comprising:

receiving a voice signal and an input signal comprising near-end environmental content;

calculating with one or more processors the near-end environmental content in the input signal;

adjusting with the one or more processors a level of a voice enhancement based at least partly on the near-end environmental content, wherein said adjusting comprises tracking the near-end environmental content when the near-end environmental content is above a threshold, and wherein the threshold is determined based at least partly on a user-adjustable noise sensitivity level; and applying the voice enhancement to the voice signal to produce an enhanced voice signal, the voice enhancement configured to emphasize one or more formants of the voice signal.

2. The method of claim 1, wherein said calculating comprises obtaining a magnitude of the near-end environmental content and smoothing the magnitude of the near-end environmental content.

3. The method of claim 1, further comprising adjusting an overall gain of the enhanced voice signal based at least partly on the near-end environmental content and on an amount of energy in the voice signal.

4. The method of claim 3, wherein said adjusting the overall gain comprises computing a gain level proportional to the near-end environmental content.

5. The method of claim 1, further comprising mapping one or more samples of the enhanced voice signal to one or more values stored in a sum of sines table to reduce clipping in the enhanced voice signal.

6. A system for automatically adjusting a voice intelligibility enhancement applied to an audio signal, the system comprising:

an enhancement module configured to receive an input voice signal comprising formants and to apply an audio enhancement to the input voice signal to provide an enhanced voice signal, the audio enhancement configured to emphasize one or more of the formants in the input voice signal;

an enhancement controller comprising one or more processors, the enhancement controller configured to adjust an amount of the audio enhancement applied by the enhancement module based at least partly on an amount of detected environmental noise by at least tracking the environmental noise when the environmental noise is above a threshold, the threshold being determined based at least partly on a user-adjustable noise sensitivity level; and an output gain controller configured to:
adjust an overall gain of the enhanced voice signal based at least partly on the amount of environmental noise and on the input voice signal, and
apply the overall gain to the enhanced voice signal to produce an amplified voice signal.

7. The system of claim 6, wherein the enhancement controller is further configured to adjust the amount of the audio enhancement applied based at least partially on a ratio of the amount of environmental noise to a threshold level.

8. The system of claim 6, wherein the enhancement module is further operative to emphasize the one or more formants by applying gains to frequency sub-bands of the input voice signal.

9. The system of claim 8, wherein the enhancement controller is further configured to adjust the amount of the audio enhancement applied by at least applying additional gains to the frequency sub-bands of the input voice signal.

10. The system of claim 6, wherein the output gain controller is further configured to adjust the overall gain by providing a gain level proportional to the amount of the environmental noise.

11. The system of claim 6, wherein the output gain controller is further configured to adjust the overall gain in response to energy of the voice signal being below a threshold.

12. The system of claim 6, further comprising a distortion control module operative to reduce clipping in the amplified voice signal.

13. Non-transitory physical computer storage having instructions stored thereon that, when executed by one or more processors, cause the one or more processors to implement a method of adjusting a voice intelligibility enhancement, the method comprising:

receiving a voice signal from a remote phone and a noise signal from a near-end microphone;

calculating a value of the noise signal;

adjusting gains applied to formants of the voice signal based at least partly on the value of the noise signal, wherein said adjusting comprises tracking the noise signal when the noise signal is above a threshold, and wherein the threshold is determined based at least partly on a user-adjustable noise sensitivity level; and applying the gains to the formants of the voice signal to produce an enhanced voice signal by emphasizing one or more formants of the voice signal.

14. The non-transitory physical computer storage of claim 13, further comprising adjusting an overall gain of the voice signal based at least partly on an amount of energy of the voice signal.

15. The non-transitory physical computer storage of claim 14, wherein the overall gain is adjusted in response to the energy of the voice signal being below a threshold.

16. A system for adjusting a sensitivity of a voice intelligibility enhancement, the system comprising:

a voice enhancement module configured to receive, with a receiving device, an input voice signal received by a receiving device from a remote device and to apply an audio enhancement to the input voice signal to emphasize one or more formants in the input voice signal;

an enhancement controller configured to adjust an amount of the audio enhancement applied by the voice enhancement module based at least partly on an amount of environmental noise present in the input voice signal; and a noise sensitivity controller comprising one or more processors configured to adjust a sensitivity of the enhancement controller to the environmental noise based at least partly on a statistical analysis of at least one or both of a microphone input signal obtained from a microphone of the receiving device and a speaker input signal provided as an output signal of the voice enhancement module, the noise sensitivity controller comprising:

a correlator configured to compute an autocorrelation of one or both of the microphone input signal and the speaker input signal, a variance module configured to estimate a variance of the autocorrelation, and a sensitivity adjuster configured to adjust the sensitivity of the enhancement controller to the environmental noise based at least partly on the estimated variance.

\* \* \* \* \*